(12) United States Patent
Shekhar et al.

(10) Patent No.: US 10,588,985 B2
(45) Date of Patent: Mar. 17, 2020

(54) COMPOSITIONS AND METHODS RELATING TO RAD6 INHIBITION

(71) Applicant: Wayne State University, Detroit, MI (US)

(72) Inventors: Malathy Shekhar, Northville, MI (US); Guangzhao Mao, Bloomfield Hills, MI (US); Yanhua Zhang, Livonia, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 15/755,386

(22) PCT Filed: Sep. 2, 2016

(86) PCT No.: PCT/US2016/050141
§ 371 (c)(1),
(2) Date: Feb. 26, 2018

(87) PCT Pub. No.: WO2017/040953
PCT Pub. Date: Mar. 9, 2017

(65) Prior Publication Data
US 2018/0280535 A1 Oct. 4, 2018

Related U.S. Application Data

(60) Provisional application No. 62/213,248, filed on Sep. 2, 2015.

(51) Int. Cl.
| | |
|---|---|
| *A61K 47/69* | (2017.01) |
| *A61K 31/53* | (2006.01) |
| *A61K 45/06* | (2006.01) |
| *A61P 35/00* | (2006.01) |

(52) U.S. Cl.
CPC .......... *A61K 47/6923* (2017.08); *A61K 31/53* (2013.01); *A61K 45/06* (2013.01); *A61P 35/00* (2018.01)

(58) Field of Classification Search
CPC ................................................. A61K 47/6923
See application file for complete search history.

(56) References Cited

U.S. PATENT DOCUMENTS

2014/0044791 A1  2/2014  Basilion et al.

FOREIGN PATENT DOCUMENTS

WO   WO-2008076883   6/2008

OTHER PUBLICATIONS

Sanders et al., Novel Inhibitors of Rad6 Ubiquitin Conjugating Enzyme: Design, Synthesis, Identification, and Functional Characterization, Molecular Cancer Therapeutics (2013), 12(4), 373-383.*
Sun et al., Engineered Nanoparticles for Drug Delivery in Cancer Therapy, Angew. Chem. Int. Ed. 2014, 53, 12320-12364.*
Chu et al., Expression of GATA3 in MDA-MB-231 Triple-negative Breast Cancer Cells Induces a Growth Inhibitory Response to TGFß, PLoS One. 2013; 8(4): e61125.*
Sanders, M. et al., Novel Inhibitors of Rad6 Ubiquitin Conjugating Enzyme: Design, Synthesis, Identification, and Functional Characterization, Molecular Cancer Therapeutics. 12: 373-383, Apr. 2013.
Rosner, K. et al., Rad6 is a Potential Early Marker of Melanoma Development, Translational Oncology, 7:384-392, May 12, 2014.
Haynes, B. et al., Gold nanoparticle conjugated Rad6 inhibitor induces cell death in triple negative breast cancer cells by inducing mitochondrial dysfunction and PARP-1 hyperactivation: Synthesis and characterization, Nanomedicine: Nanotechnology, Biology and Medicine, 12: 745-757, Nov. 10, 2015.

* cited by examiner

*Primary Examiner* — Svetlana M Ivanova
(74) *Attorney, Agent, or Firm* — Julie K. Stable; Dinsmore & Shohl LLP

(57) ABSTRACT

Pharmaceutical compositions, methods of treatment of proliferative diseases and commercial packages are provided according to aspects of the present invention which relate to a first therapeutic agent coupled to a nanoparticle, wherein the first therapeutic agent is SMI #8 or SMI #9 a pharmaceutically acceptable salt, ester, amide, stereoisomer, hydrate, or derivative of either thereof. According to particular aspects, the SMI #8 or SMI #9 is conjugated to gold nanoparticles.

17 Claims, 13 Drawing Sheets

| Treatment | MDA-MB-468 (GI50) | HCC1937 (GI50) |
|---|---|---|
| Cisplatin | 3.8 μM | >25 μM |
| SMI#9-GNP | >10 μM | >10 μM |
| SMI#9-GNP + Cisplatin | 0.8 μM | 4.9 μM |

COMPOSITIONS AND METHODS RELATING TO RAD6 INHIBITION

REFERENCE TO RELATED APPLICATION

This application claims priority to U.S. Provisional Patent Application Ser. No. 62/213,248, filed Sep. 2, 2015, the entire content of which is incorporated herein by reference.

FIELD OF THE INVENTION

According to general aspects, the present invention relates to compositions and methods for treatment of cancer. In particular aspects, the present invention relates to compositions and methods for treatment of cancer using nanoparticle-conjugated drugs.

BACKGROUND OF THE INVENTION

Despite recent medical progress, cancer continues to be one of the most common and deadly diseases. There is a continuing need for compositions and methods to treat cancer.

SUMMARY OF THE INVENTION

Pharmaceutical compositions are provided according to aspects of the present invention which include a first therapeutic agent coupled to a nanoparticle, wherein the first therapeutic agent is SMI #8 or SMI #9, a pharmaceutically acceptable salt, ester, amide, stereoisomer, hydrate, or derivative of either thereof. Optionally included is a pharmaceutically acceptable carrier. Further optionally included is an additional therapeutic agent. Further optionally included is an additional anti-cancer agent. The additional therapeutic agent is optionally coupled to the same nanoparticle as the first therapeutic agent or to a different nanoparticle.

Pharmaceutical compositions are provided according to aspects of the present invention which include a first therapeutic agent coupled to a gold nanoparticle (GNP), wherein the first therapeutic agent is SMI #8 or SMI #9, a pharmaceutically acceptable salt, ester, amide, stereoisomer, hydrate, or derivative of either thereof. Optionally included is a pharmaceutically acceptable carrier. Further optionally included is an additional therapeutic agent. Further optionally included is an additional anti-cancer agent. The additional therapeutic agent is optionally coupled to the same gold nanoparticle as the first therapeutic agent or to a different nanoparticle which may be gold or another nanoparticle type.

Pharmaceutical compositions are provided according to aspects of the present invention which include cisplatin and a first therapeutic agent coupled to a nanoparticle, wherein the first therapeutic agent is SMI #8 or SMI #9, a pharmaceutically acceptable salt, ester, amide, stereoisomer, hydrate, or derivative of either thereof. Optionally included is a pharmaceutically acceptable carrier. The cisplatin is optionally coupled to the same nanoparticle as the first therapeutic agent or to a different nanoparticle.

Pharmaceutical compositions are provided according to aspects of the present invention which include cisplatin and a first therapeutic agent coupled to a gold nanoparticle (GNP), wherein the first therapeutic agent is SMI #8 or SMI #9, a pharmaceutically acceptable salt, ester, amide, stereoisomer, hydrate, or derivative of either thereof. Optionally included is a pharmaceutically acceptable carrier. The cisplatin is optionally coupled to the same gold nanoparticle as the first therapeutic agent or to a different nanoparticle which may be gold or another nanoparticle type.

According to aspects of the present invention, a derivative of SMI #8 included in compositions is:

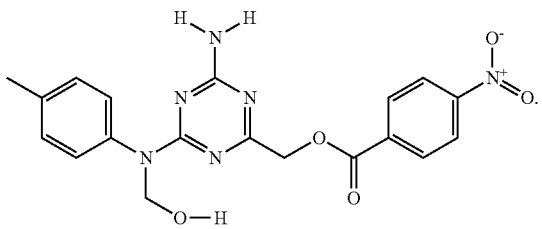 [SMILES: Cc1ccc(N(CO)c2nc(N)nc(COC(=O)c3ccc([N+](=O)[O-])cc3)n2)cc1]

According to aspects of the present invention, a derivative of SMI #9 included in compositions is:

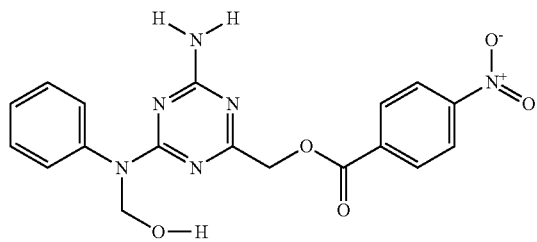 [SMILES: Nc1nc(COC(=O)c2ccc([N+](=O)[O-])cc2)nc(N(CO)c2ccccc2)n1]

Methods of treating a subject having a proliferative disorder are provided according to aspects of the present invention which include administering a therapeutically effective dose of a pharmaceutical composition which includes a first therapeutic agent coupled to a nanoparticle, wherein the first therapeutic agent is SMI #8 or SMI #9 a pharmaceutically acceptable salt, ester, amide, stereoisomer, hydrate, or derivative of either thereof. Optionally included in the pharmaceutical composition is a pharmaceutically acceptable carrier. Further optionally included is an additional therapeutic agent. The additional therapeutic agent can be an anti-cancer agent. The additional therapeutic agent is optionally coupled to the same nanoparticle type as the first therapeutic agent or to a different nanoparticle type.

Methods of treating a subject having a proliferative disorder are provided according to aspects of the present invention which include administering a therapeutically effective dose of a pharmaceutical composition which includes a first therapeutic agent coupled to a gold nanoparticle (GNP), wherein the first therapeutic agent is SMI #8 or SMI #9, a pharmaceutically acceptable salt, ester, amide, stereoisomer, hydrate, or derivative of either thereof. Optionally included in the pharmaceutical composition is a pharmaceutically acceptable carrier. Further optionally included is an additional therapeutic agent. The additional therapeutic agent can be an anti-cancer agent. The additional therapeutic agent is optionally coupled to the same gold nanoparticle as the first therapeutic agent or to a different nanoparticle which may be gold or another nanoparticle type.

Methods of treating a subject having a proliferative disorder are provided according to aspects of the present invention which include administering a therapeutically effective dose of a combination of cisplatin and a pharmaceutical composition which includes a first therapeutic agent coupled to a nanoparticle, wherein the first therapeutic agent is SMI #8 or SMI #9, a pharmaceutically acceptable salt, ester, amide, stereoisomer, hydrate, or derivative of either thereof. Optionally included in the pharmaceutical composition is a pharmaceutically acceptable carrier. The cisplatin is optionally coupled to the same nanoparticle type as the first therapeutic agent or to a different nanoparticle type. The cisplatin is optionally included in the pharmaceutical composition with the first therapeutic agent or separately and may be administered at the same time or a different time.

Methods of treating a subject having a proliferative disorder are provided according to aspects of the present invention which include administering a therapeutically effective dose of a combination of cisplatin and a pharmaceutical composition which includes a first therapeutic agent coupled to a gold nanoparticle (GNP), wherein the first therapeutic agent is SMI #8 or SMI #9, a pharmaceutically acceptable salt, ester, amide, stereoisomer, hydrate, or derivative of either thereof. Optionally included in the pharmaceutical composition is a pharmaceutically acceptable carrier. The cisplatin is optionally coupled to the same gold nanoparticle as the first therapeutic agent or to a different nanoparticle which may be gold or another nanoparticle type.

When administered separately, the cisplatin may be administered before or after the first therapeutic agent, such as 1, 2, 3, 4, 5, 10, 15, 20, 30, 60 minutes before or after, or 2, 4, 6, 12, or 24 hours before or after. A synergistic effect of administration of the cisplatin and first therapeutic effect allows for a lower than typical amount of cisplatin and the first therapeutic agent to be used to achieve a therapeutic benefit.

According to aspects of methods of treating a subject having a proliferative disorder of the present invention, the proliferative disorder is characterized by overexpression and/or overactivity of Rad6.

According to aspects of methods of treating a subject having a proliferative disorder of the present invention, the proliferative disorder is characterized by resistance to an anti-cancer agent.

According to aspects of methods of treating a subject having a proliferative disorder of the present invention, the proliferative disorder is melanoma.

According to aspects of methods of treating a subject having a proliferative disorder of the present invention, the proliferative disorder is breast cancer.

According to aspects of methods of treating a subject having a proliferative disorder of the present invention, the proliferative disorder is triple negative breast cancer.

According to aspects of methods of treating a subject having a proliferative disorder of the present invention, administering a therapeutically effective dose of a pharmaceutical composition includes administering a pharmaceutical composition including a derivative of SMI #8 having the chemical structure:

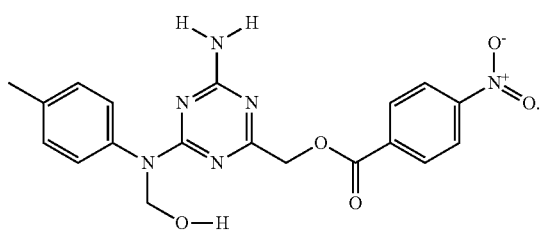 [SMILES: Cc1ccc(N(CO)c2nc(N)nc(COC(=O)c3ccc([N+](=O)[O-])cc3)n2)cc1]

According to aspects of methods of treating a subject having a proliferative disorder of the present invention, administering a therapeutically effective dose of a pharmaceutical composition includes administering a pharmaceutical composition including a derivative of SMI #9 having the chemical structure:

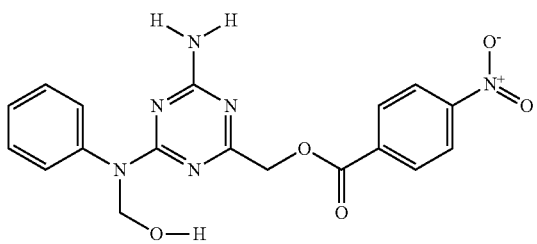 [SMILES: Nc1nc(COC(=O)c2ccc([N+](=O)[O-])cc2)nc(N(CO)c2ccccc2)n1]

Commercial packages are provided according to aspects of the present invention which include a first therapeutic agent coupled to a nanoparticle, wherein the first therapeutic agent is SMI #8 or SMI #9 a pharmaceutically acceptable salt, ester, amide, stereoisomer, hydrate, or derivative of either thereof. Optionally included is a pharmaceutically acceptable carrier. Further optionally included is an additional therapeutic agent. The additional therapeutic agent can be an anti-cancer agent. The additional therapeutic agent is optionally coupled to the same nanoparticle as the first therapeutic agent or to a different nanoparticle.

Commercial packages are provided according to aspects of the present invention which include a first therapeutic agent coupled to a gold nanoparticle, wherein the first therapeutic agent is SMI #8 or SMI #9 a pharmaceutically acceptable salt, ester, amide, stereoisomer, hydrate, or derivative of either thereof. Optionally included is a pharmaceutically acceptable carrier. Further optionally included is an additional therapeutic agent. The additional therapeutic agent can be an anti-cancer agent. The additional therapeutic agent is optionally coupled to the same nanoparticle as the first therapeutic agent or to a different nanoparticle.

Commercial packages are provided according to aspects of the present invention which include cisplatin and a first therapeutic agent coupled to a nanoparticle, wherein the first therapeutic agent is SMI #8 or SMI #9 a pharmaceutically acceptable salt, ester, amide, stereoisomer, hydrate, or derivative of either thereof. Optionally included is a pharmaceutically acceptable carrier. Further optionally included is an additional anti-cancer agent. The cisplatin is optionally coupled to the same nanoparticle type as the first therapeutic agent or to a different nanoparticle type.

Commercial packages are provided according to aspects of the present invention which include cisplatin and a first therapeutic agent coupled to a gold nanoparticle, wherein the first therapeutic agent is SMI #8 or SMI #9 a pharmaceutically acceptable salt, ester, amide, stereoisomer, hydrate, or derivative of either thereof. Optionally included is a pharmaceutically acceptable carrier. The cisplatin is optionally coupled to the same gold nanoparticle type as the first therapeutic agent or to a different nanoparticle type.

A derivative of SMI #8 included in a commercial package according to aspects of the present invention is:

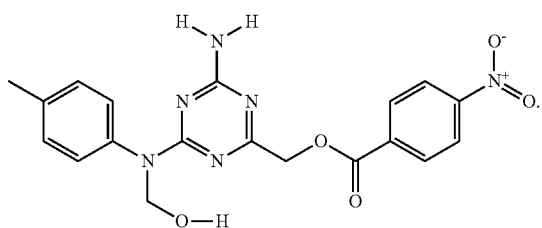 [SMILES: Cc1ccc(N(CO)c2nc(N)nc(COC(=O)c3ccc([N+](=O)[O-])cc3)n2)cc1]

A derivative of SMI #9 included in a commercial package according to aspects of the present invention is:

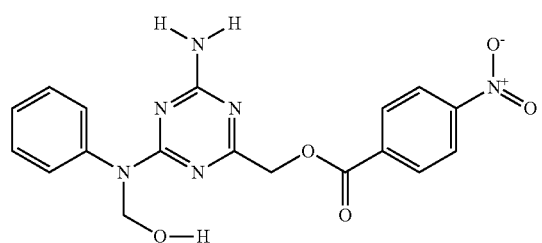 [SMILES: Nc1nc(COC(=O)c2ccc([N+](=O)[O-])cc2)nc(N(CO)c2ccccc2)n1]

DETAILED DESCRIPTION OF THE INVENTION

Figure 1A:
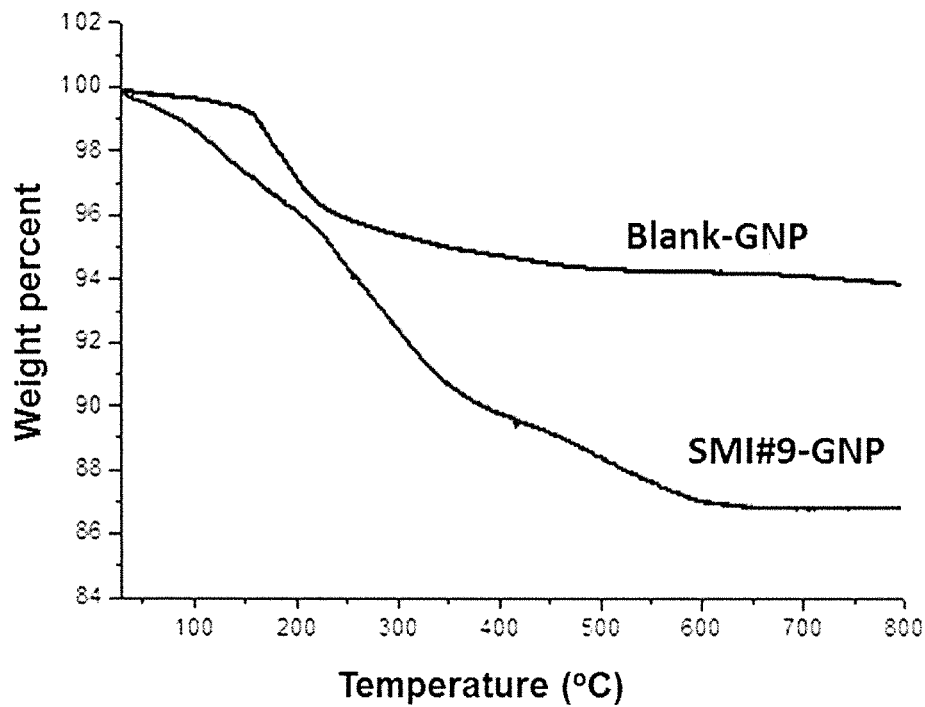
FIG. 1A is a graph showing the TGA curves of MSA-GNP (blank-GNP) and MSA-GNP conjugated SMI #9 (SMI #9-GNP) with weight loss of 6.15% and 13%, respectively, at 800° C.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Chu, E. and Devita, V. T., Eds., Physicians' Cancer Chemotherapy Drug Manual, Jones & Bartlett Publishers, 2005; J. M. Kirkwood et al., Eds., Current Cancer Therapeutics, 4th Ed., Current Medicine Group, 2001; Remington: The Science and Practice of Pharmacy, Lippincott Williams & Wilkins, 21st Ed., 2005; L. V. Allen, Jr. et al., Ansel's Pharmaceutical Dosage Forms and Drug Delivery Systems, 8th Ed., Philadelphia, Pa.: Lippincott, Williams & Wilkins, 2004; and L. Brunton et al., Goodman & Gilman's The Pharmacological Basis of Therapeutics, McGraw-Hill Professional, 12th Ed., 2011.

The singular terms "a," "an," and "the" are not intended to be limiting and include plural referents unless explicitly stated otherwise or the context clearly indicates otherwise.

Compositions and methods for treating cancer are provided according to the present invention.

Compositions according to aspects of the present invention inhibit cancer cell multiplication and tumor development and are considered useful as chemotherapeutic agents.

Compositions and methods according to aspects described herein are useful to inhibit cancer cells in vitro and in vivo.

Particular cancers treated using methods and compositions described herein are characterized by abnormal cell proliferation including, but not limited to, pre-neoplastic hyperproliferation, cancer in-situ, neoplasms and metastasis. Methods and compositions of the present invention can be used for amelioration of signs and/or symptoms of cancer. The terms "treating" and "treatment" used to refer to treatment of a cancer in a subject include: inhibiting or ameliorating the cancer in the subject, such as slowing progression of the cancer and/or reducing or ameliorating a sign or symptom of the cancer.

Compositions and methods for treating cancer are provided according to the present invention which inhibit Rad6.

Pharmaceutical compositions including:

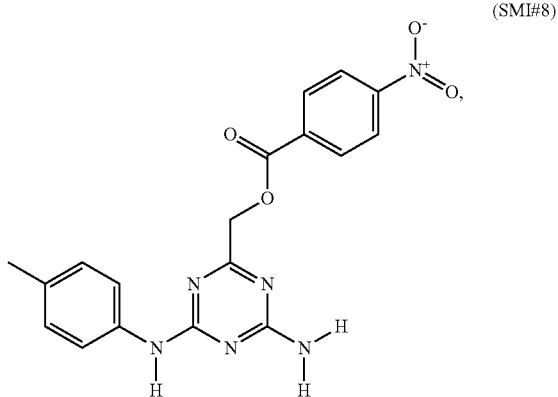 [SMILES: Cc1ccc(Nc2nc(N)nc(COC(=O)c3ccc([N+](=O)[O-])cc3)n2)cc1]

(SMI#8)

a pharmaceutically acceptable salt, ester, amide, stereoisomer, hydrate, or derivative thereof, coupled to a nanoparticle are provided according to aspects disclosed herein. SMI #8, a pharmaceutically acceptable salt, ester or derivative thereof, coupled to a nanoparticle is termed SMI #8-NP herein. SMI #8, a pharmaceutically acceptable salt, ester or derivative thereof, coupled to a gold nanoparticle is termed SMI #8-GNP herein.

Pharmaceutical compositions including:

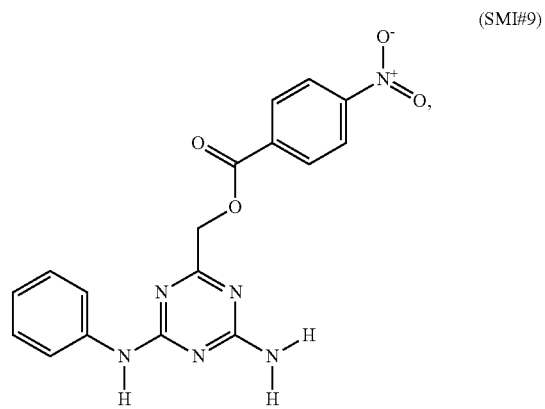 [SMILES: Nc1nc(COC(=O)c2ccc([N+](=O)[O-])cc2)nc(Nc2ccccc2)n1]

(SMI#9)

a pharmaceutically acceptable salt, ester, amide, stereoisomer, hydrate, or derivative thereof, coupled to a nanoparticle are provided according to aspects of the present invention. SMI #9, a pharmaceutically acceptable salt, ester or derivative thereof, coupled to a nanoparticle is termed SMI #9-NP herein. SMI #9, a pharmaceutically acceptable salt, ester or derivative thereof, coupled to a gold nanoparticle is termed SMI #9-GNP herein.

The term "derivative" as used herein refers to a compound that is modified compared to a first compound and which has similar or improved bioactivity compared to the first compound.

Compositions according to the present invention encompass stereoisomers of chemical structures shown and/or described herein. Compositions according to the present invention encompass the individual enantiomers of the compounds having chemical structures shown and/or described herein, as well as wholly or partially racemic mixtures of any of these.

A pharmaceutical composition includes SMI #8-NP or a pharmaceutically acceptable salt thereof; and a pharmaceutically acceptable carrier in particular aspects of the present invention.

A pharmaceutical composition includes SMI #9-NP or a pharmaceutically acceptable salt thereof; and a pharmaceutically acceptable carrier in particular aspects of the present invention.

Compositions including mixtures of SMI #8-NP and SMI #9-NP are specifically contemplated and are considered to be within the scope of the present invention.

The term "pharmaceutically acceptable carrier" refers to a carrier which is substantially non-toxic to a subject to which the composition is administered and which is substantially chemically inert with respect to the active component or components.

Binding of SMI #8 and/or SMI #9 to nanoparticles is achieved by any of various methods effective to bond a composition to a nanoparticle, illustratively including adsorption and chemical bonding, to produce SMI #8-NP and SMI #9-NP.

SMI #8 and/or SMI #9 can be bonded directly to one or more functional groups of the particles or indirectly bonded to the nanoparticles, for example, via bonding to a coating or linker disposed on the nanoparticles.

SMI #8 and/or SMI #9 can be modified to include a functional group for use in bonding to nanoparticles, thereby producing a therapeutically active derivative of the parent compound. For example, SMI #8 and/or SMI #9 can be modified to include one or more carboxyl, amine, amino, carboxylate, halide, ester, alcohol, carbamide, aldehyde, chloromethyl, sulfur oxide, nitrogen oxide, epoxy, maleimide, alkene, azide, alkyne and/or tosyl functional groups for use in binding the modified SMI #8 and/or SMI #9 to nanoparticles.

According to particular aspects, SMI #8 is modified to include an alcohol functional group to produce the therapeutically active derivative, SMI #8-mod, having the structural formula:

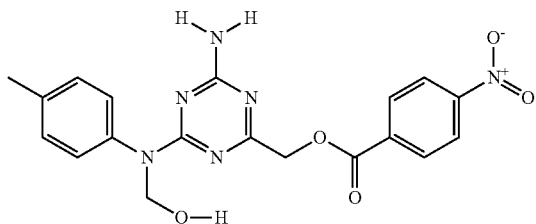 [SMILES: Cc1ccc(N(CO)c2nc(N)nc(COC(=O)c3ccc([N+](=O)[O-])cc3)n2)cc1]

According to particular aspects, SMI #9 is modified to include an alcohol functional group to produce the therapeutically active derivative, SMI #9-mod, having the structural formula:

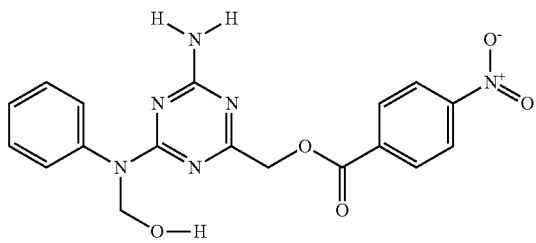 [SMILES: Nc1nc(COC(=O)c2ccc([N+](=O)[O-])cc2)nc(N(CO)c2ccccc2)n1]

Nanoparticles to which amplicons are bound can be any solid or semi-solid nanoparticles to which amplicons can be attached, which are suitable for a multiplex assay and which are stable and insoluble under hybridization and detection conditions. The nanoparticles can be of any shape, such as cylindrical, spherical, and so forth, size, composition, or physiochemical characteristics. The nanoparticle size or composition can be chosen so that the particle can be separated from fluid, e.g., on a filter with a particular pore size or by some other physical property, e.g., a magnetic property.

Nanoparticles can have a diameter from about 1 nanometer (nm) to about 1,000 nm in diameter, inclusive, for example, a size ranging from about 5-500 nm, inclusive, 10-100 nm, inclusive, or 15-50 nm, inclusive.

Nanoparticles may be organic or inorganic, such as glass or metal and can be nanoparticles of a synthetic or naturally occurring polymer, such as polystyrene, polycarbonate, silicon, nylon, cellulose, agarose, dextran, and polyacrylamide.

Nanoparticles are gold nanoparticles according to aspects of the present invention.

Nanoparticles can naturally include functional groups of be modified to include functional groups for binding to SMI #8 and/or SMI #9. For example, nanoparticles can include carboxyl, amine, amino, carboxylate, halide, ester, alcohol, carbamide, aldehyde, chloromethyl, sulfur oxide, nitrogen oxide, epoxy, maleimide, alkene, azide, alkyne and/or tosyl functional groups.

Functional groups, modification of substances to include functional groups and binding of functional groups, are known in the art, for example as described in Fitch, R. M., Polymer Colloids: A Comprehensive Introduction, Academic Press, 1997. In a particular example, 1-ethyl-3-[3-dimethylaminopropyl]carbodiimide hydrochloride, EDC or EDAC chemistry, can be used to attach SMI #8 and/or SMI #9 to nanoparticles as described herein.

SMI #8-NP and SMI #9-NP are prodrug compositions provided according to aspects of the present invention and administered to a subject in need thereof according to methods of treatment described herein.

The term "prodrug" as used herein refers to compositions that are transformed in vivo to yield a therapeutically active compound. This transformation may occur, for example, by hydrolysis of an ester group or other biologically labile group.

SMI #8-GNP and SMI #9-GNP are prodrug compositions provided according to aspects of the present invention and administered to a subject in need thereof according to methods of treatment described herein.

According to aspects of the present invention, SMI #8-mod is a therapeutically active derivative of SMI #8 released by hydrolysis in vivo from SMI #8-NP.

According to aspects of the present invention, SMI #8-mod is a therapeutically active derivative of SMI #8 released by hydrolysis in vivo from SMI #8-GNP.

According to aspects of the present invention, SMI #9-mod is a therapeutically active derivative of SMI #9 released by hydrolysis in vivo from SMI #9-NP.

According to aspects of the present invention, SMI #9-mod is a therapeutically active derivative of SMI #9 released by hydrolysis in vivo from SMI #9-GNP.

Optionally, a targeting agent is conjugated to nanoparticles in addition to SMI #8, SMI #9, a pharmaceutically acceptable salt, ester or derivative of either or both thereof.

In a further option, an additional therapeutic agent is conjugated to nanoparticles in addition to SMI #8, SMI #9, a pharmaceutically acceptable salt, ester or derivative of either or both thereof.

A pharmaceutical composition according to the invention generally includes about 0.1-99% of SMI #8, a pharmaceutically acceptable salt, ester or derivative thereof coupled to a nanoparticle and/or SMI #9, a pharmaceutically acceptable salt, ester or derivative thereof coupled to a nanoparticle.

Pharmaceutical compositions suitable for delivery to a subject may be prepared in various forms illustratively including physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Additional components illustratively including a buffer, a solvent, or a diluent may be included.

Such formulations are administered by a suitable route including parenteral and oral administration. Administration may include systemic or local administration, such as systemic or local injection. According to particular aspects of the present invention, administration is by systemic administration, particularly intravenous injection.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature. Prolonged delivery of an injectable pharmaceutical form can be brought about by the use of agents delaying absorption, for example, aluminum monostearate and gelatin.

Solid dosage forms for oral administration include capsules, tablets, pills, powders, and granules. In such solid dosage forms, one or more anti-cancer compounds described herein is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include a buffering agent.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include a pharmaceutically acceptable carrier formulated as an emulsion, solution, suspension, syrup, or elixir. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to SMI #8-NP and/or SMI #9-NP, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and the like.

In particular aspects, SMI #8-NP and/or SMI #9-NP are formulated for topical application.

In further particular aspects, SMI #8-NP and/or SMI #9-NP are formulated for topical application and are characterized by less than 10% absorption of an active ingredient in the composition into the system of an individual treated topically. In still further particular aspects, SMI #8-NP and/or SMI #9-NP are formulated for topical application and are characterized by less than 9%, 8%, 7%, 6%, 5%, 4%, 3%, 2%, 1% absorption of an active ingredient in the composition into the system of an individual treated topically.

Absorption into the system of an individual can be measured by any of various methods, particularly assay for the active ingredient, a metabolite and/or a breakdown product of the active ingredient in a sample obtained from an individual treated with the topical formulation. For example, a blood, plasma or serum sample can be assayed for presence of the active ingredient, a metabolite of the active ingredient and/or a breakdown product of the active ingredient.

A topical formulation can be an ointment, lotion, cream or gel in particular aspects. Topical dosage forms such as ointment, lotion, cream or gel bases are described in Remington: The Science and Practice of Pharmacy, $21^{st}$ Ed., Lippincott Williams & Wilkins, 2006, p. 880-882 and p. 886-888; and in Allen, L. V. et al., Ansel's Pharmaceutical Dosage Forms and Drug Delivery Systems, $8^{th}$ Ed., Lippincott Williams & Wilkins, 2005, p. 277-297.

Pharmaceutically acceptable carriers and formulation of pharmaceutical compositions are known in the art, illustratively including, but not limited to, as described in Remington: The Science and Practice of Pharmacy, $21^{st}$ Ed., Lippincott, Williams & Wilkins, Philadelphia, Pa., 2006; and Allen, L. V. et al., Ansel's Pharmaceutical Dosage Forms and Drug Delivery Systems, $8^{th}$ h Ed., Lippincott, Williams & Wilkins, Philadelphia, Pa., 2005.

Pharmaceutical compositions including SMI #8-NP and/or SMI #9-NP are administered to treat a subject having cancer, including melanoma, liver cancer, prostate cancer, breast cancer, brain cancer, stomach cancer, pancreatic cancer, blood cancers including leukemia, bone marrow cancer, lymphatic cancer, uterine cancer, cervical cancer, ovarian cancer, lung cancer, colon cancer, and cancers of connective tissues (sarcomas) and other soft tissues according to aspects of the present invention.

Pharmaceutical compositions including SMI #8-NP and/or SMI #9-NP are administered to treat a subject having triple negative breast cancer according to aspects of the present invention.

Pharmaceutical compositions including SMI #8-NP and/or SMI #9-NP are administered topically to treat a subject having melanoma according to aspects of the present invention.

The term "pharmaceutically acceptable salt" refers to salts which are suitable for use in a subject without undue toxicity or irritation to the subject and which are effective for their intended use.

Pharmaceutically acceptable salts include pharmaceutically acceptable acid addition salts and base addition salts. Pharmaceutically acceptable salts are well-known in the art, such as those detailed in S. M. Berge et al., J. Pharm. Sci., 66:1-19, 1977. Exemplary pharmaceutically acceptable salts are those suitable for use in a subject without undue toxicity or irritation to the subject and which are effective for their intended use which are formed with inorganic acids such as hydrochloric acid, hydrobromic acid, hydroiodic acid, nitric acid, phosphoric acid, sulfuric acid and sulfamic acid; organic acids such as acetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, formic acid, fumaric acid, glutamic acid, glycolic acid, glycerophosphoric acid, hemisulfic acid, heptanoic acid, hexanoic acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, trichloroacetic acid, trifluoroacetic acid and undecanoic acid; inorganic bases such as ammonia, hydroxide, carbonate, and bicarbonate of ammonium; organic bases such as Primary, secondary, tertiary and quaternary amine compounds ammonium, arginine, betaine, choline, caffeine, diolamine, diethylamine, diethanolamine, 2-dimethylaminoethanol, 2-diethylaminoethanol, dicyclohexylamine, dicyclohexylamine, dibenzylamine, N, N-dibenzylphenethylamine, 1-ephenamine, N, N'-dibenzylethylenediamine, ethanolamine, ethylamine, ethylenediamine, glucosamine, histidine, hydrabamine, isopropylamine, 1h-imidazole, lysine, methylamine, N-ethylpiperidine, N-methylpiperidine, N-methylmorpholine, N, N-dimethylaniline, piperazine, trolamine, methylglucamine, purines, piperidine, pyridine, theobromine, tetramethylammonium compounds, tetraethylammonium compounds, trimethylamine, triethylamine, tripropylamine and tributylamine and metal cations such as aluminum, calcium, copper, iron, lithium, magnesium, manganese, potassium, sodium, and zinc.

Combination Treatments

Combinations of therapeutic agents are administered according to aspects of the present invention.

In some aspects, SMI #8-NP and SMI #9-NP of the present invention are both administered to a subject to treat cancer in a subject in need thereof.

In further aspects, at least one of SMI #8-NP and SMI #9-NP and at least one additional therapeutic agent are administered to a subject to treat cancer in a subject in need thereof.

In still further aspects, at least one of SMI #8-NP and SMI #9-NP and at least two additional therapeutic agents are administered to a subject to treat cancer in a subject in need thereof.

The term "additional therapeutic agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included in aspects of methods and compositions of the present invention include, but are not limited to, antibiotics, antivirals, antineoplastic agents, analgesics, antipyretics, antidepressants, antipsychotics, anti-cancer agents, antihistamines, anti-osteoporosis agents, anti-osteonecrosis agents, anti-inflammatory agents, anxiolytics, chemotherapeutic agents, diuretics, growth factors, hormones, non-steroidal anti-inflammatory agents, steroids and vasoactive agents.

Combination therapies utilizing one or both of SMI #8-NP and SMI #9-NP and one or more additional therapeutic agents may show synergistic effects, e.g., a greater therapeutic effect than would be observed using SMI #8-NP, SMI #9-NP or one or more additional therapeutic agents alone as a monotherapy.

According to aspects, combination therapies include: (1) pharmaceutical compositions that include SMI #8-NP and/or SMI #9-NP in combination with one or more additional therapeutic agents; and (2) co-administration of SMI #8-NP and/or SMI #9-NP with one or more additional therapeutic agents wherein SMI #8-NP and/or SMI #9-NP and the one or more additional therapeutic agents have not been formulated in the same composition. When using separate formulations, the SMI #8-NP and/or SMI #9-NP may be administered at the same time, intermittent times, staggered times, prior to, subsequent to, or combinations thereof, with reference to the administration of the one or more additional therapeutic agents.

Combination treatments can allow for reduced effective dosage and increased therapeutic index of SMI #8-NP and/or SMI #9-NP and the one or more additional therapeutic agents used in methods of the present invention.

According to aspects of the present invention, methods of treating a subject having cancer includes administration of SMI #8-NP and/or SMI #9-NP in combination with cisplatin. According to aspects of the present invention, methods of treating a subject having cancer includes administration of SMI #8-GNP and/or SMI #9-GNP in combination with cisplatin.

Optionally, a method of treating a subject having cancer further includes an adjunct anti-cancer treatment. An adjunct anti-cancer treatment can be administration of an anti-cancer agent.

Anti-cancer agents are described, for example, in Goodman et al., Goodman and Gilman's The Pharmacological Basis of Therapeutics, 8th Ed., Macmillan Publishing Co., 1990.

Anti-cancer agents illustratively include abiraterone acetate, acivicin, aclarubicin, acodazole, acronine, adozelesin, afatinib, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, axitinib, azacitidine, azetepa, azotomycin, batimastat, belinostat, bendamustine, benzodepa, bevacizumab, bexarotene, bicalutamide, bisantrene, bisnafide dimesylate, bizelesin, bleomycin, bortezomib, bosutinib, brentuximab, brequinar, bropirimine, busulfan, cabazitaxel, cactinomycin, calusterone, capecitabine, caracemide, carbetimer, carboplatin, carfilzomib, carmustine, carubicin, carzelesin, cedefingol, celecoxib, ceritinib, cetuximab, chlorambucil, cirolemycin, cisplatin, cladribine, clofarabine, crisnatol mesylate, crizotinib, cyclophosphamide, cytarabine, dabrafenib, dacarbazine, dactinomycin, dasatinib, daunorubicin, decitabine, degarelix, denosumab, dexrazoxane hydrochloride, dexormaplatin, dezaguanine, dezaguanine mesylate, diaziquone, dinutuximab, docetaxel, doxorubicin, droloxifene, dromostanolone, duazomycin, edatrexate, eflomithine, elsamitrucin, enloplatin, enpromate, enzalutamide, epipropidine, epirubicin, erbulozole, eribulin mesylate, erlotinib hydrochloride, esorubicin, estramustine, etanidazole, etoposide, etoprine, everolimus, exemestane, fadrozole, fazarabine, fenretinide, floxuridine, fludarabine, fluorouracil, flurocitabine, fosquidone, fostriecin, fulvestrant, gefitinib, gemcitabine, glucarpidase, goserelin acetate, hydroxyurea, ibrutinib, idarubicin, idelalisib, ifosfamide, ilmofosine, imatinib mesylate, imiquimod, interleukin II (IL-2, including recombinant interleukin II or rIL2), interferon alfa-2a, interferon alfa-2b, interferon alfa-n1, interferon alfa-n3, interferon beta-1a, interferon gamma-1b, ipilimumab, iproplatin, irinotecan, ixabepilone, lanreotide, lapatinib, lenalidomide, lenvatinib, letrozole, leucovorin calcium, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nilotinib, nivolumab, nocodazole, nogalamycin, obinutuzumab, olaparib, omacetaxine mepesuccinate, ondansetron hydrochloride, ormnaplatin, oxaliplatin, oxisuran, paclitaxel, palbociclib, palifermin, panitumumab, panobinostat, pazopanib hydrochloride, pegaspargase, peliomycin, pembrolizumab, pemetrexed, pentamustine, peplomycin, perfosfamide, pertuzumab, pipobroman, piposulfan, piroxantrone hydrochloride, plerixafor, plicamycin, plomestane, pomalidomide, ponatinib hydrochloride, porfimer, porfiromycin, pralatrexate, prednimustine, procarbazine, puromycin, pyrazofurin, raloxifene hydrochloride, ramucirumab, rasburicase, regorafenib, riboprine, rogletimide, romidepsin, ruxolitinib, safingol, semustine, siltuximab, simtrazene, sonidegib, sorafenib, sparfosate, sparsomycin, spirogermanium, spiromustine, spiroplatin, streptonigrin, streptozocin, sulofenur, sunitinib, talisomycin, tamoxifen, tecogalan, tegafur, teloxantrone, temoporfin, temozolomide, temsirolimus, teniposide, teroxirone, testolactone, thalidomide, thiamiprine, thioguanine, thiotepa, tiazofurin, tirapazamine, topotecan, toremifene, trametinib, trastuzumab, trestolone, triciribine, trimetrexate, triptorelin, tubulozole, uracil mustard, uredepa, vandetanib, vapreotide, vemurafenib, verteporfin, vinblastine, vincristine sulfate, vindesine, vinepidine, vinglycinate, vinleurosine, vinorelbine, vinrosidine, vinzolidine, vismodegib, vorinostat, vorozole, zeniplatin, zinostatin, zoledronate, zoledronic acid, and zorubicin.

An adjunct anti-cancer treatment can be a radiation treatment of a subject or an affected area of a subject's body.

Methods of treating a subject are provided according to aspects of the present invention which include administering a therapeutically effective amount of SMI #8-NP to a subject in need thereof, wherein the subject has an abnormal proliferative condition, such as cancer, pre-neoplastic hyperproliferation, cancer in-situ, neoplasms, metastasis, tumor or benign growth.

Methods of treating a subject are provided according to aspects of the present invention which include administering a therapeutically effective amount of SMI #9-NP to a subject in need thereof, wherein the subject has an abnormal proliferative condition, such as cancer, pre-neoplastic hyperproliferation, cancer in-situ, neoplasms, metastasis, tumor or benign growth.

Subjects for treatment are identified as having cancer using well-known medical and diagnostic techniques.

The term "subject" refers to an individual in need of treatment for a pathological condition responsive to the beneficial effects of compositions of the present invention, particularly cancer, and generally includes mammals and birds, such as, but not limited to, humans, other primates, cats, dogs, cows, horses, rodents, pigs, sheep, goats and poultry. According to aspects of the present invention, the subject is human.

A pharmaceutical composition according to the present invention is suitable for administration to a subject by a variety of systemic and/or local routes including, but not limited to, intravenous, intramuscular, subcutaneous, intraperitoneal, oral, otic, rectal, vaginal, topical, parenteral, pulmonary, ocular, nasal, intratumoral and mucosal.

According to aspects of the present invention, compositions of the present invention are formulated for systemic administration.

An inventive pharmaceutical composition may be administered acutely or chronically. For example, a composition as described herein may be administered as a unitary dose or in multiple doses over a relatively limited period of time, such as seconds—hours. In a further embodiment, administration may include multiple doses administered over a period of days—years, such as for chronic treatment of cancer.

A therapeutically effective amount of a pharmaceutical composition according to the present invention will vary depending on the particular pharmaceutical composition used, the severity of the condition to be treated, the species of the subject, the age and sex of the subject and the general physical characteristics of the subject to be treated. One of skill in the art could determine a therapeutically effective amount in view of these and other considerations typical in medical practice. In general it is contemplated that a therapeutically effective amount would be in the range of about 0.001 mg/kg-100 mg/kg body weight, optionally in the range of about 0.01-10 mg/kg, and further optionally in the range of about 0.1-5 mg/kg. Further, dosage may be adjusted depending on whether treatment is to be acute or continuing.

A therapeutically effective amount of a pharmaceutical composition of the present invention is an amount which has a beneficial effect in a subject being treated. In subjects having cancer, such as a condition characterized by abnormal cell proliferation including, but not limited to, pre-neoplastic hyperproliferation, cancer in-situ, neoplasms, metastasis, a tumor, a benign growth or other condition responsive to an inventive pharmaceutical composition, a therapeutically effective amount of the pharmaceutical composition is effective to ameliorate or prevent one or more signs and/or symptoms of the condition. For example, a therapeutically effective amount of a composition is effective to detectably increase apoptosis and/or decrease proliferation of cells of a cancer condition characterized by abnormal cell proliferation including, but not limited to, pre-neoplastic hyperproliferation, cancer in-situ, neoplasms, metastasis, a tumor, a benign growth or other condition responsive to an inventive composition.

In particular aspects, cancers treated in a subject using methods and compositions described herein are characterized by overexpression or overactivity of Rad6. The terms "overexpression" and "overactivity" are used herein to describe increased levels or activity, respectively, of Rad6 compared to a standard.

Increased levels or activity of Rad6 is determined, for instance, by measurement of gene copy number, protein or RNA levels in cells known or suspected to be dysplastic, pre-cancerous, cancerous, metastatic or otherwise characterized by abnormal cell proliferation compared to normal cells. Assays for increased levels or activity of Rad6 include, but are not limited to, ubiquitination assays, immunoassays and nucleic acid assays.

Standards are well-known in the art and the standard used can be any appropriate standard. In one example, a standard is an amount of the biomarker present in a comparable sample from a control subject. A standard may be a reference level of Rad6 previously determined in a sample of an individual subject or in a population and stored in a print or electronic medium for recall and comparison to an assay result.

A standard can be an amount of the biomarker present in a comparable sample obtained from the same subject at a different time. For example, a standard can be an amount of Rad6 present in a comparable sample obtained from the same subject at a different time.

A standard can be an average level of a biomarker described herein present in comparable samples of one or more populations. The "average level" is determined by assay of the biomarker in comparable samples obtained from each member of the population. The term "comparable sample" is used to indicate that the samples are of the same type, i.e. each of the comparable samples is a cell or tissue sample, for example.

Assay results can be analyzed using statistical analysis by any of various methods, exemplified by parametric or non-parametric tests, analysis of variance, analysis of covariance, logistic regression for multivariate analysis, Fisher's exact test, the chi-square test, Student's T-test, the Mann-Whitney test, Wilcoxon signed ranks test, McNemar test, Friedman test and Page's L trend test. These and other statistical tests are well-known in the art as detailed in Hicks, C M, Research Methods for Clinical Therapists: Applied Project Design and Analysis, Churchill Livingstone (publisher); $5^{th}$ Ed., 2009; and Freund, R J et al., Statistical Methods, Academic Press; $3^{rd}$ Ed., 2010.

Commercial Packages

Commercial packages are provided according to aspects of the present invention for treating cancer in a subject in need thereof, including SMI #8-NP and/or SMI #9-NP; or a pharmaceutically acceptable salt, stereoisomer, hydrate, amide or ester thereof. One or more auxiliary components are optionally included in commercial packages of the present invention, such as a pharmaceutically acceptable carrier exemplified by a buffer, diluent or a reconstituting agent.

Embodiments of inventive compositions and methods are illustrated in the following examples. These examples are provided for illustrative purposes and are not considered limitations on the scope of inventive compositions and methods.

Examples

Synthesis of Gold Nanoparticle (GNP) and Conjugation of Rad6 Inhibitor SMI #9 to GNP SMI #9 was synthesized as described in Sanders M A et al., Mol Cancer Ther 2013; 12:373-83.

For the production of SMI #9-tethered GNPs, citrate-reduced GNPs were synthesized from $HAuCl_4 \cdot 3H_2O$ and subsequently capped by MSA. Modified SMI #9 was attached to the MSA-GNP surface via ester bond as shown in Scheme 1 in FIG. 13.

Mercaptosuccinic acid-capped GNP (MSA-GNP) was synthesized as described in Turkevich J et al., Discuss Faraday Soc 1951; 55-75; Kimling J et al., J Phys Chem B 2006; 110:15700-7; Frens G., Kolloid Z Z Polym 1972; 250:736-41; Frens G., Nature Phys Sci 1973; 241:20-2; and Jana N R et al., J Phys Chem B 2001; 105:4065-7. Briefly described, ice-cold 0.1 M $NaBH_4$ solution was added with vigorous stirring to a solution of 0.25 mM $HAuCl_4 \cdot 3H_2O$ and 0.25 mM trisodium citrate. The pH was adjusted to 11, and 50 mg MSA was added. The final solution was concentrated to 2.5 g (gold)/L by centrifugation using 10,000 MW Amicon filters.

SMI #9 was modified to enable GNP conjugation via an ester bond. To modify SMI #9, 1.5 mg SMI #9 was dissolved in 0.5 ml tetrahydrofuran (THF; 50%, v/v) followed by addition of 10 mg of $NaHCO_3$ and 2.6 mg di-tert-butyl dicarbonate $(Boc)_2O$. After 30 min reaction, 5 μl of HCHO and 5 μl of triethylamine ($Et_3N$) were added and the hydroxymethylation reaction was allowed to proceed for 48 hours. The solution was then added to GNP (2.5 g/L gold concentration) solution. The pH of the solution was adjusted to 4.7, and 2 mg 1-ethyl-3-(3-dimethylaminopropyl)carbodiimide (EDC), 0.2 mg 4-dimethylaminopyridine (DMAP), and 2 ml dimethyl sulfoxide (DMSO) were added to catalyze the esterification reaction as shown in Scheme 1. After 40 hours, the final solution was concentrated to 0.2 g/ml.

Characterization of GNP and GNP-Drug Conjugates

SMI #9 conjugated to GNP was characterized by thermogravimetric analysis (TGA) on a SDT-Q600 Thermo-Gravity Analyser using air as the supporting gas. The air flow rate was maintained at 100 ml/min, and the sample was heated from 25 to 800° C. at a heating rate of 10° C./min. GNP solutions were also characterized by UV-vis spectroscopy with a Varian Cary® 50 spectrometer in 2 mm optical path cells, and by transmission electron microscopy (TEM) at 200 kV with a JEOL JEM-2010 microscope equipped with a Gatan multiscan CCD camera. Transmission electron microscopy (TEM) samples were prepared by placing a droplet of the GNP solution on a Formvar-coated copper grid. Excess liquid was removed by filter paper placed under the grid and air dried. Dynamic light scattering (DLS) and zeta potential were measured using a Malvern Nano-ZS. The Z-average hydrodynamic diameter (HD), polydispersity index (PDI) and zeta potential were measured at 25° C. 15 scans were performed in each measurement. The backscattering angle $\Theta$ was fixed at 1720 with a laser wavelength λ=633 nm. The size measurement range was set between 1 nm and 6 μm. HD is a function of the diffusion coefficient (D), temperature (T), and viscosity (η) according to the Stokes-Einstein equation:

$$HD = \frac{kT}{3\pi \eta D},$$

k is Boltzmann constant, T is 25° C., and D was obtained from autocorrelation function via the cumulant fitting. Atomic force microscopy (AFM) imaging was conducted using a Dimension 3100 AFM from VEECO. AFM tapping mode in liquid was used, and the nanoconjugate was deposited on mica by spin coating.

FIG. 1A shows the TGA curves of MSA-GNP (blank-GNP) and MSA-GNP conjugated SMI #9 (SMI #9-GNP) with weight loss of 6.15% and 13%, respectively, at 800° C. A 4 nm in diameter GNP contains ~2,000 gold atoms with a molecular weight of 390,000. The weight loss of 6.15% for MSA-GNP corresponds to a surface coverage of 170 MSA molecules per GNP or molecular area of 29.4 $nm^2$ per MSA. The 13% weight loss for MSA-GNP with conjugated SMI #9 corresponds to gold:MSA:SMI #9 weight ratio of 100: 6.6:8.3. It is therefore estimated that there are 82 hydroxymethylated $C_{17}N_6H_{14}O_4$(SMI #9) molecules per 4 nm GNP based on the total SMI #9 weight of 32,370. This indicates that 24% of all possible —COOH reactive sites on the GNP are conjugated with SMI #9, and corresponds to a conjugation efficiency of 42% as calculated from the feed ratio.

Figure 1B:
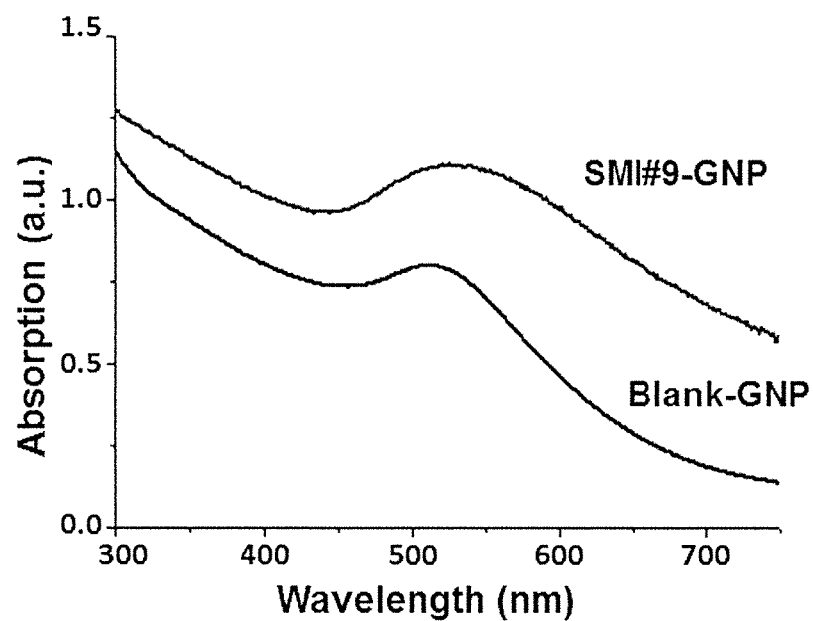
FIG. 1B is a graph showing the UV-vis spectra of gold nanoparticles (GNP) before and after conjugation with modified SMI #9 (SMI #9-mod)
Figure 1C:
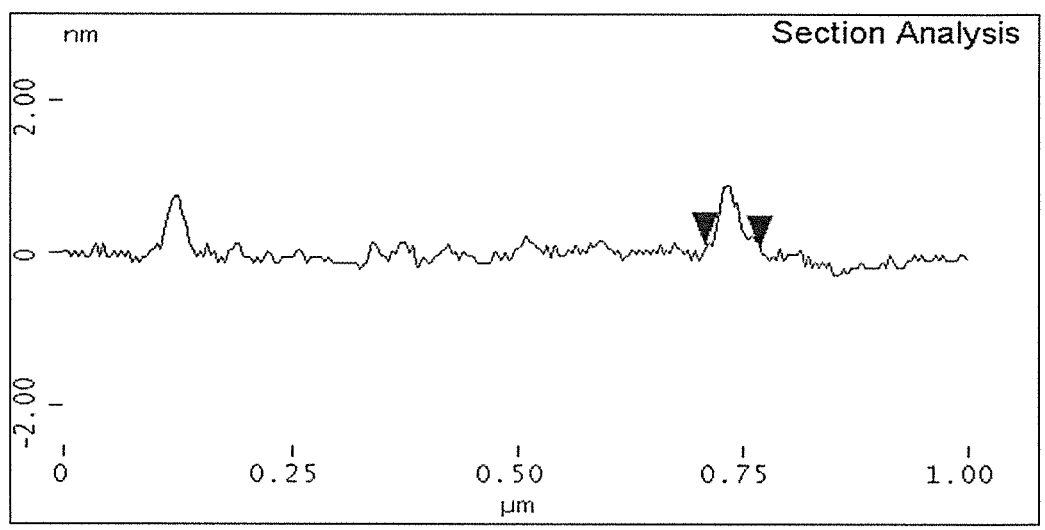
FIG. 1C is a graph showing results of atomic force microscopic analysis of SMI #9-GNP.

FIG. 1B shows the UV-vis spectra of GNPs before and after conjugation with modified SMI #9 (SMI #9-mod). The surface plasmon resonance (SPR) absorption peak of freshly prepared GNPs is 508 nm, which corresponds to GNP diameter range of 3-5 nm. However, upon conjugation with modified SMI #9, the SPR absorption peak broadened and shifted to 524 nm, which is indicative of particle aggregation. The size of SMI #9-GNPs was also determined by TEM and AFM which showed a size of 32 nm and 40.2±1.4 nm, respectively, that is consistent with aggregation. DLS further verified the average size of SMI #9-GNP nanoconjugate at 41 nm. The zeta potential of MSA-capped GNP changed from −41 mV to −16.2 mV after conjugation with SMI #9. The decrease in surface charge is the result of SMI #9 conjugation to highly charged MSA. Particle aggregation could also contribute to surface charge reduction.

SMI #9 and SMI #9-GNP Uptake and Intracellular Release of the Free Drug from GNP Conjugate MDA-MB-231 cells were plated at a density of $3 \times 10^5$ cells in 35 mm dishes and exposed to various doses of SMI #9-GNP or untreated for 24-48 h. Cultures were rinsed, and lysed by freeze-thaw cycles in cold hypotonic buffer, and clarified by centrifugation at 10×000 g. Aliquots of clarified cell lysates were analysed by FTIR spectroscopy using untreated cell lysates spiked with free SMI #9 as reference. To determine intracellular release of modified SMI #9 from nanoparticles, SUM1315 ($2 \times 10^6$ cells/100 mm dish) cells were exposed for 8 or 24 h to 5 µM free SMI #9, 5 µM SMI #9-GNP or the corresponding amount of blank-GNP, or untreated. Cultures were rinsed several times in ice-cold phosphate buffered saline (PBS), lysed with cold 80% methanol and clarified by centrifugation at 10,000 g for 10 min at 4° C. The supernatant was collected and an aliquot was subjected to high performance liquid chromatography (HPLC) coupled with tandem mass spectrometry (LC-MS/MS) analysis. Chromatographic analysis was performed using a Waters Model 2695 separations system (Milford, Mass., USA). Separation was achieved on a Waters Xterra MS C18 column (50×2.1 mm i.d., 3.5 µm), using an isocratic mobile phase consisting of methanol/0.45% formic acid in water (60:30, v/v) at a flow rate of 0.2 mL/min. The column effluent was monitored using a Waters Quattro Micro™ triple quadrupole mass-spectrometric detector (Milford, Mass., USA). Multiple reaction monitoring (MRM) at positive ionization mode were chosen for the analyte detection. Mass spectrometric parameters were optimized for the detection of SMI #9, with the cone voltage of 45 V and collision energy of 24 V. Samples were introduced into the ionization source through a heated nebulized probe (350° C.) with 500 L/hour desolvation nitrogen gas flow. For the detection of SMI #9, the spectrometer was programmed to monitor the transition of the parent ion, m/Z 366.69 ([M+H]+), to the major daughter ion with m/Z 150.1, FIG. 3B. For the detection of modified SMI #9 released from GNP, 14 MS transitions, including m/z 366.69>150.1, 368.86>150.7, 381.3>150.1, 381.3>150.7, 381.3>232.3, 381.3>248.3, 397.3>150.1, 397.3>150.7, 397.3>232.3, 397.3>248.3, 379.4>150.1, 379.4>150.7, 379.4>232.3, 379.4>248.3, were monitored based on possible hypothetical drug release mechanisms. All the chosen parent ions were selected in the first quadrupole and allowed to pass into the collision cell filled with argon gas with a pressure of 0.00172 mBar. The dwell time per channel was set to 0.01 s for data collection.

Intracellular SMI #9-GNP Uptake and Release

Figure 2A:
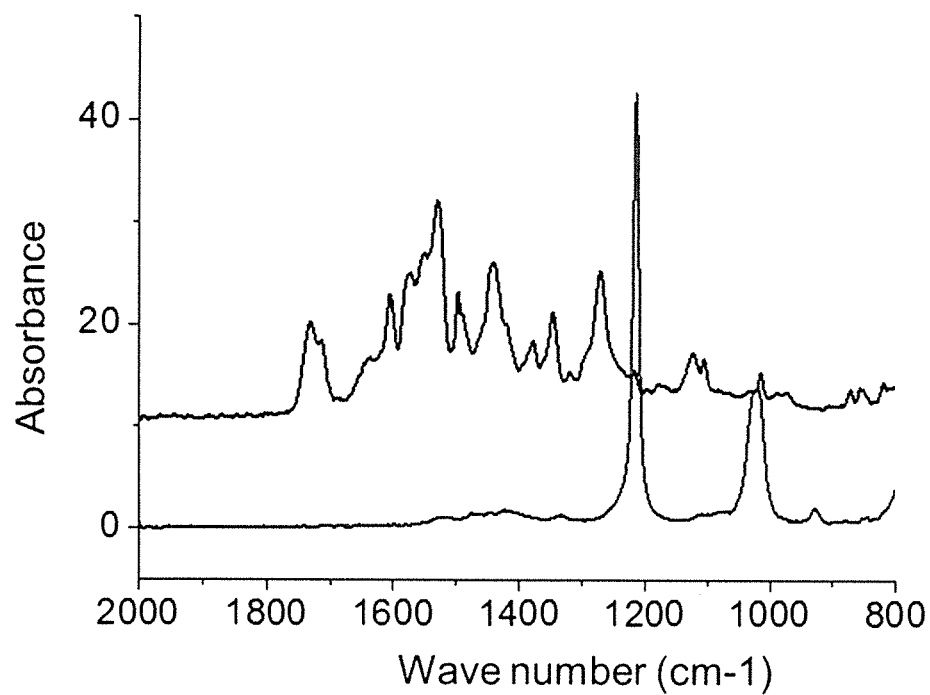
FIG. 2A is a graph showing results of FTIR analysis of SMI #9.
Figure 2B:
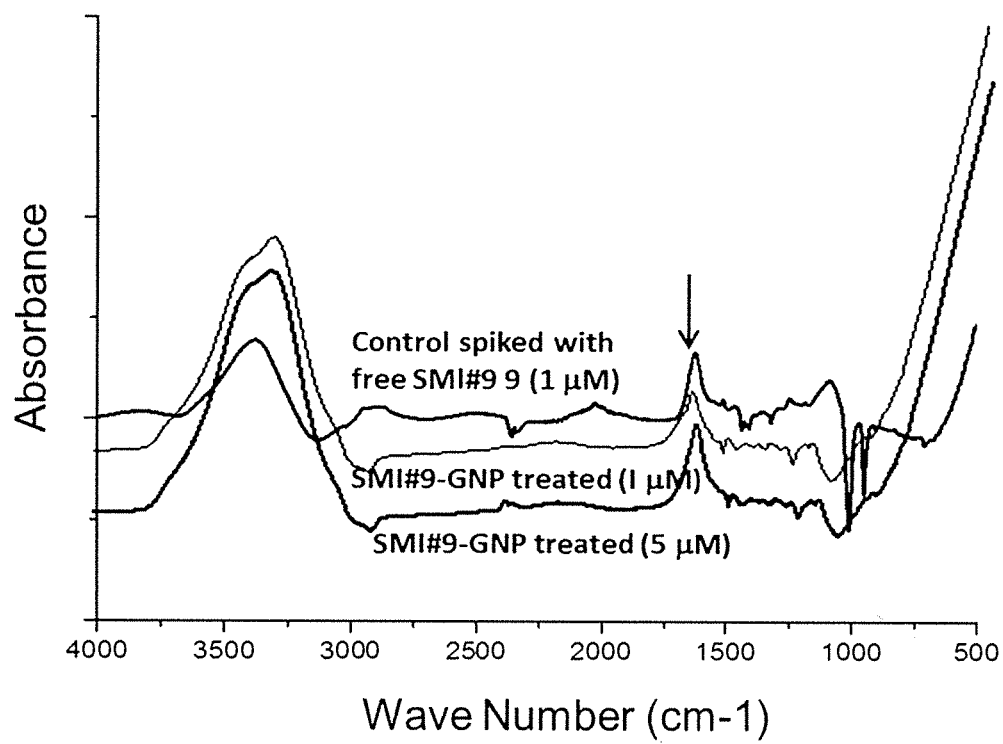
FIG. 2B is a graph showing results of FTIR analysis of lysates prepared from SMI #9-GNP treated MDA-MB-231 cells or MDA-MB-231 control lysates spiked with SMI #9 showed characteristic nitro group banding at ~1550 cm$^{-1}$, indicative of SMI #9 presence.

To determine SMI #9-GNP uptake and intracellular release of the conjugated SMI #9, MDA-MB-231 or SUM1315 cells were exposed to SMI #9-GNP, blank-GNP, SMI #9 or untreated, and cell lysates analyzed by FTIR or LC-MS/MS. Control cell lysates spiked with (parent) SMI #9 were included as reference controls. FTIR analysis of SMI #9 (FIG. 2A), and lysates prepared from SMI #9-GNP treated MDA-MB-231 cells or MDA-MB-231 control lysates spiked with SMI #9 showed characteristic nitro group banding at ~1550 cm$^{-1}$, indicative of SMI #9 presence (FIG. 2B).

Figure 3A:
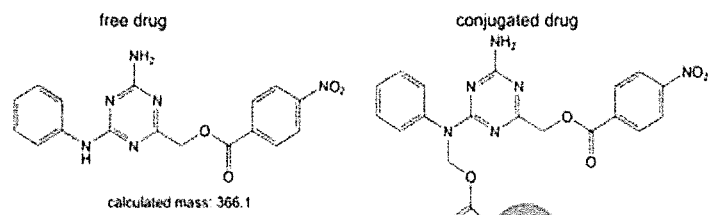
FIG. 3A is a chemical structure drawing showing SMI #9 (free drug) compared to SMI #9-NP (conjugated drug)
Figure 3B:
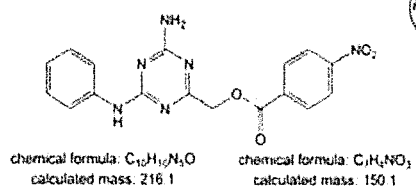
FIG. 3B is a chemical structure drawing showing intracellular hydrolysis releasing modified SMI #9.
Figure 3C:
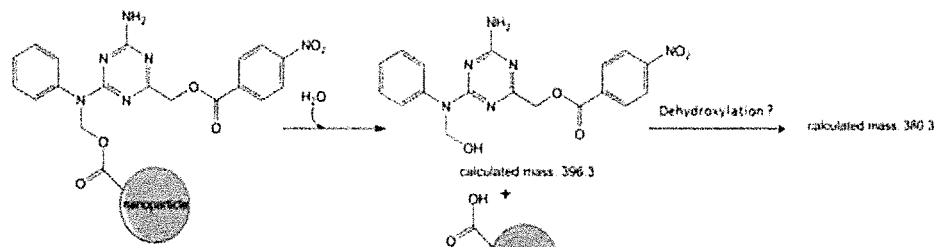
FIG. 3C is a chemical structure drawing showing intracellular hydrolysis releasing modified SMI #9.
Figure 3D:
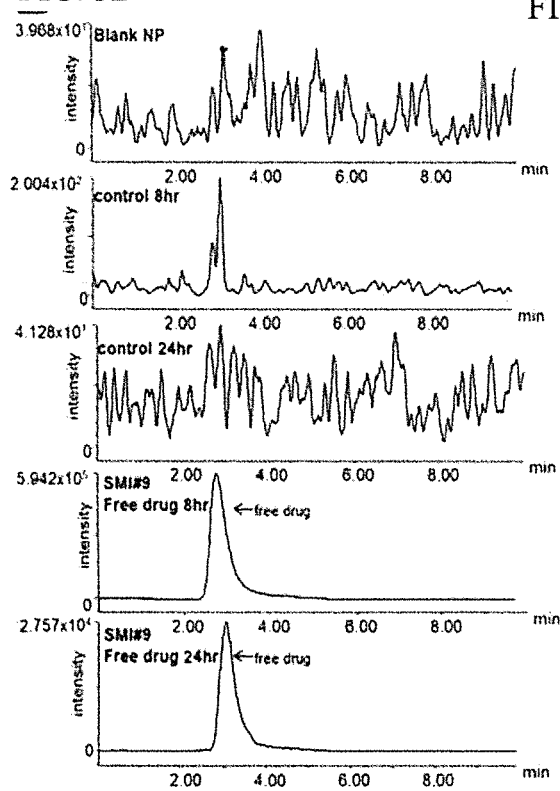
FIG. 3D shows mass spectroscopy analysis results in which positive control cells treated with free (parent) SMI #9 showed the expected peak under m/z 366.69>150.1 transition.
Figure 3E:
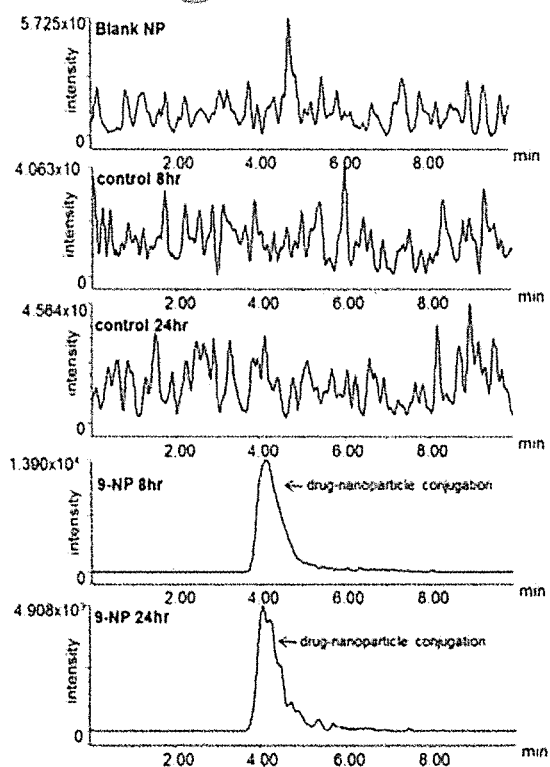
FIG. 3E shows mass spectroscopy analysis results and among the various MS transitions analyzed a strong peak was detected only under m/z 381.3>150.1 transition in SMI #9-GNP treated cells (at both 8 and 24 h) but not in blank-GNP or control cultures.
Figure 13:
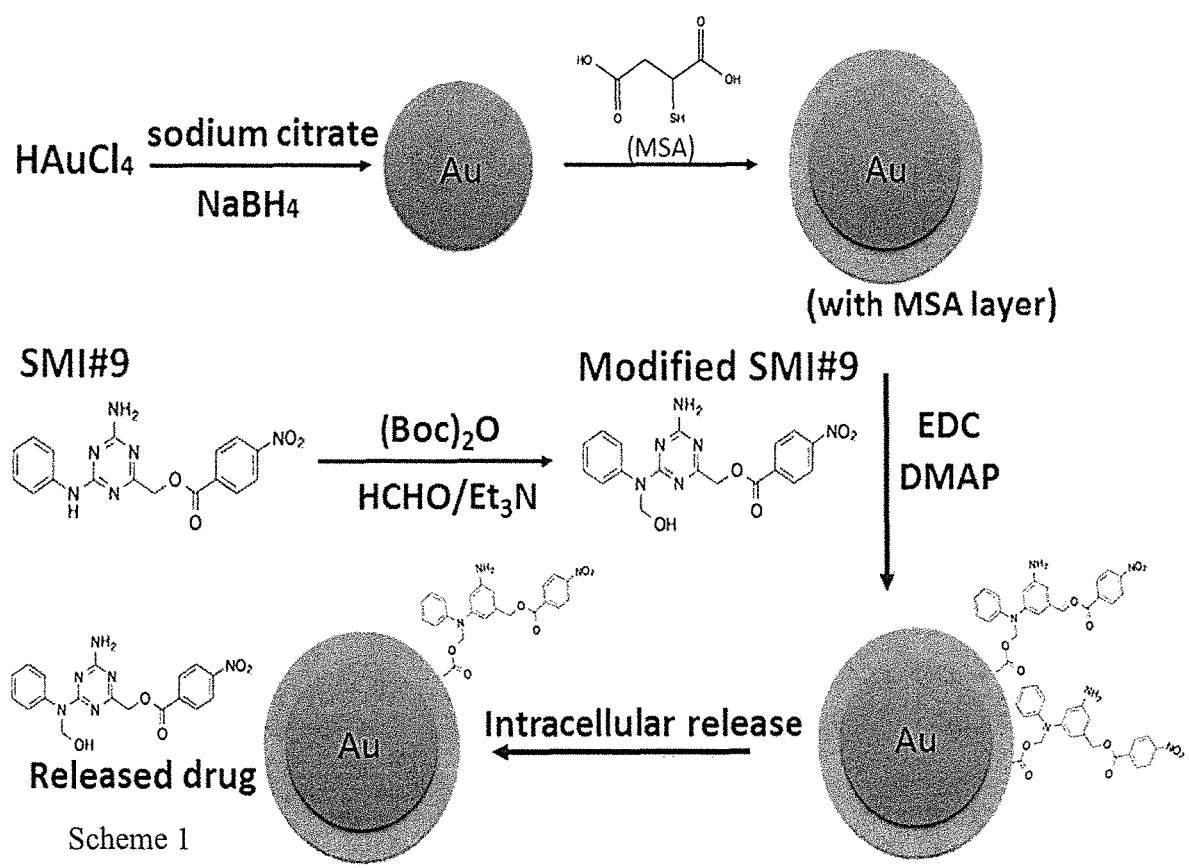
FIG. 13 shows a scheme for synthesis of SMI #9-tethered GNPs (SMI #9-GNP).

SMI #9 was modified to enable conjugation to GNP via an ester bond as shown in Scheme 1 in FIG. 13 and FIG. 3A. Intracellular hydrolysis would result in release of modified SMI #9 with the molecular weight of 396.3, which would theoretically produce parent ions at 397.3 ([M+H]+) and product ions at 150.1, see FIGS. 3A, 3B and 3C. No peak was detected under the transition of 397.3>150.1 in SMI #9-GNP treated cells. Among the various MS transitions analyzed a strong peak was detected only under m/z 381.3>150.1 transition in SMI #9-GNP treated cells (at both 8 and 24 h) but not in blank-GNP or control cultures, FIG. 3E. Release of drug with 381.3 molecular mass could theoretically arise by dehydroxylation; however, the precise structure of intracellularly released drug and its metabolic processing is under investigation. The peak signals were stronger at 8 hours as compared to 24 hours, indicating rapid intracellular processing. The positive control cells treated with free (parent) SMI #9 showed the expected peak under m/z 366.69>150.1 transition, FIG. 3D. These results indicate efficient uptake and rapid intracellular processing of the SMI #9-GNP conjugates.

Cell Survival Assay

MDA-MB-231, SUM-1315, MDA-MB-468, and HCC1937 TNBC cells (ATCC) were maintained in Dulbecco's Modified Eagle's Medium (DMEM)/F-12 supplemented with 5% fetal bovine serum. Nontransformed MCF10A human breast cells were maintained in DMEM/F12 supplemented with 5% horse serum, 20 ng/ml epidermal growth factor, 10 µg/ml insulin, 0.5 µg/ml hydrocortisone and 0.10 µg/ml cholera toxin. Sensitivity to SMI #9-GNP was assessed by trypan blue staining or MTT colorimetric assay. Briefly, cells were seeded in 96-well plates at a density of $5-7 \times 10^3$ cells per well and allowed to attach overnight. Cells were treated with free SMI #9, SMI #9-GNP, or blank-GNP at various concentrations in triplicates for 72 hours. In some cases, treatments included various doses of cisplatin singly or in combination with SMI #9-GNP. On the final day, medium was replaced with drug free medium, incubated with MTT at 37° C. for 2-3 hours. The medium and MTT were removed, and the MTT-formazan crystals dissolved in 200 µl of 0.04 N HCl/isopropanol, and absorbance measured at 570 nm using the Synergy 2 multi-well plate reader. Alternately, cultures were trypsinized and cell viability determined by trypan blue exclusion using the Biorad TC10 automatic cell counter. At least two to three independent experiments were performed for each cell line.

Cellular Response to SMI #9-Conjugated GNP

The sensitivities of MDA-MB-231, SUM1315, HCC-1937, and MDA-MB-468 TNBC cells, and nontransformed MCF10A human breast cells to SMI #9-GNP as compared to blank-GNP, or free (parent) SMI #9 were determined by MTT or trypan blue staining assays. Whereas all TNBC cell lines are growth inhibited by free SMI #9 with GI50s for MDA-MB-231, SUM1315, HCC1937 and MDA-MB-468 of 5 µM, 6 µM, 1.8 µM and 3 µM, respectively, these cell lines display variable sensitivities to SMI #9-GNP (FIG. 4A-4D). Blank-GNP added at amounts equivalent to 1 or 10 µM SMI #9-GNP demonstrated negligible cytotoxicity in all four lines. MCF10A cells were unaffected by free SMI #9 (12) and SMI #9-GNP (FIG. 4E). Among the TNBC lines, SUM1315 cells displayed greatest sensitivity to SMI #9-GNP with GI50 (based on the concentration of SMI #9) of ~0.5 µM as compared to 8.2 µM for MDA-MB-231 cells. Both HCC1937 and MDA-MB-468 cells were unaffected by SMI #9-GNP. Consistent with the MTT assay results, simultaneous phase contrast imaging showed drug-induced morphologic transformations in the sensitive cells. In HCC1937 and MDA-MB-468 cells that are unaffected by SMI #9-GNP, the GNPs appeared to aggregate at the cell surface. When combined with cisplatin, however, SMI #9-GNP synergistically increased cisplatin sensitivity of MDA-MB-468 and HCC1937 cells (FIG. 4F). These data indicate that once imported into the cells, SMI #9-GNP is therapeutically active in basal subtype TNBC cells.

Acridine Orange/Ethidium Bromide Staining

Since MTT assays (FIG. 4A-4D) showed variable SMI #9-GNP induced growth inhibitory effects in the TNBC lines, it was determined whether these sensitivities resulted from a cytostatic or cytotoxic response. Cells undergoing apoptosis/necrosis were detected by the differential uptake of the fluorescent DNA binding dyes acridine orange and ethidium bromide. Breast cancer cells ($10 \times 10^3$) were seeded on cover slips and treated with vehicle, free SMI #9, blank-GNP or SMI #9-GNP for 24-48 hours. Following treatment, cover slips were rinsed with PBS and stained with ethidium bromide/acridine orange (each 25 µg/ml). Stained cells were imaged with an Olympus BX40 fluorescence microscope. A minimum of six different fields with at least 50 cells/field were scored for determination of acridine orange/ethidium bromide uptake (12).

SMI #9-GNP Sensitivity is Associated with Apoptosis

Figure 4A:
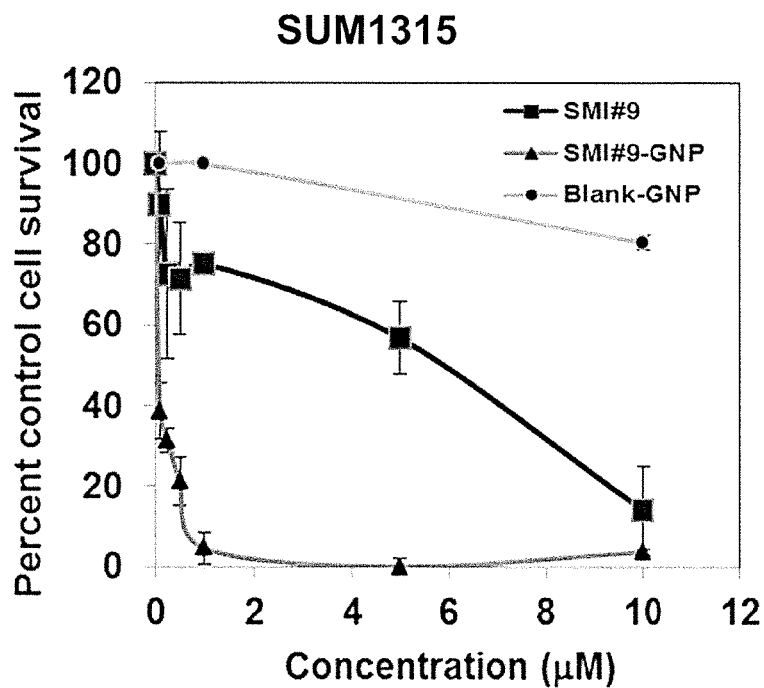
FIG. 4A is a graph showing sensitivity of SUM1315 triple negative breast cancer (TNBC) cells to SMI #9-GNP as compared to blank-GNP, or free (parent) SMI #9.
Figure 4B:
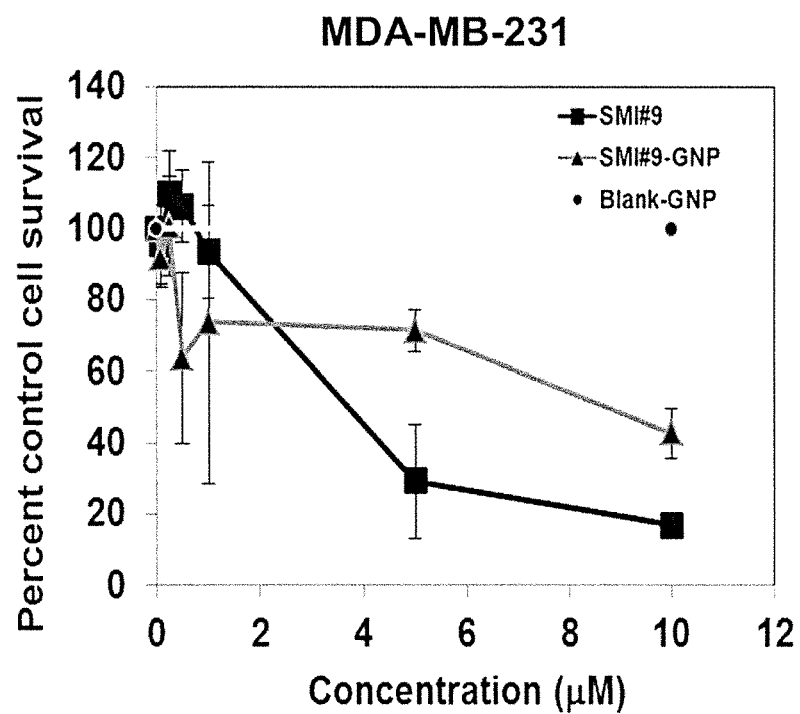
FIG. 4B is a graph showing sensitivity of MDA-MB-231 TNBC cells to SMI #9-GNP as compared to blank-GNP, or free (parent) SMI #9.
Figure 4C:
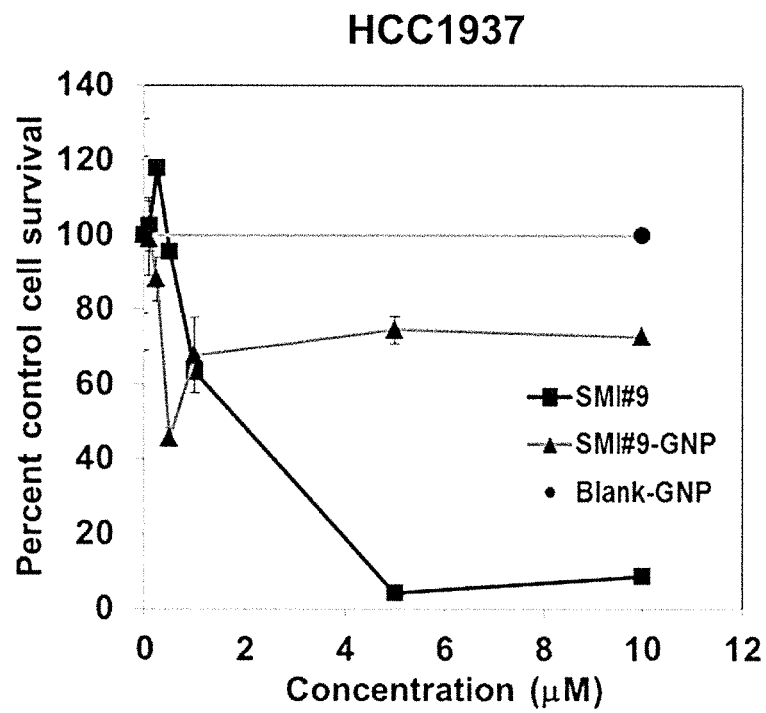
FIG. 4C is a graph showing sensitivity of HCC-1937 TNBC cells to SMI #9-GNP as compared to blank-GNP, or free (parent) SMI #9.
Figure 4D:
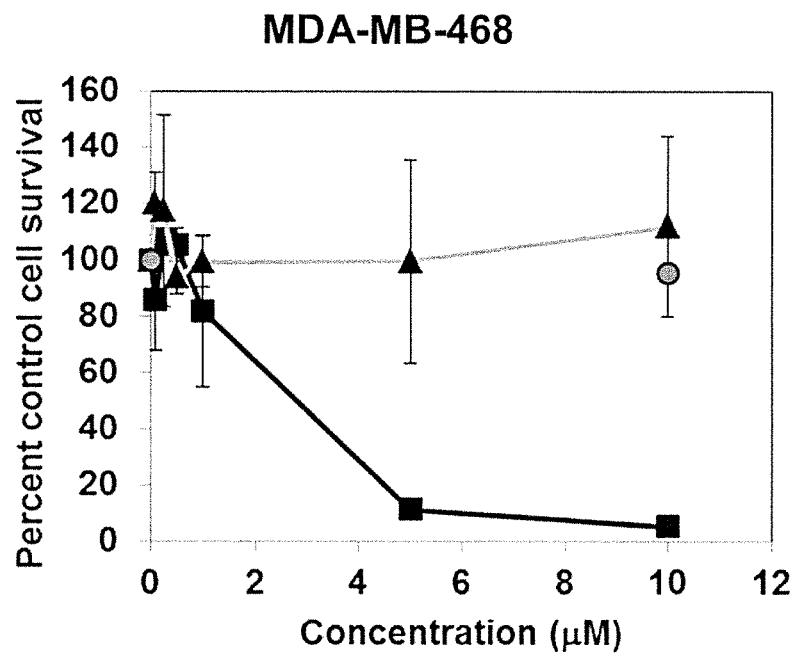
FIG. 4D is a graph showing sensitivity of MDA-MB-468 TNBC cells to SMI #9-GNP as compared to blank-GNP, or free (parent) SMI #9.
Figures 4E, 4F:
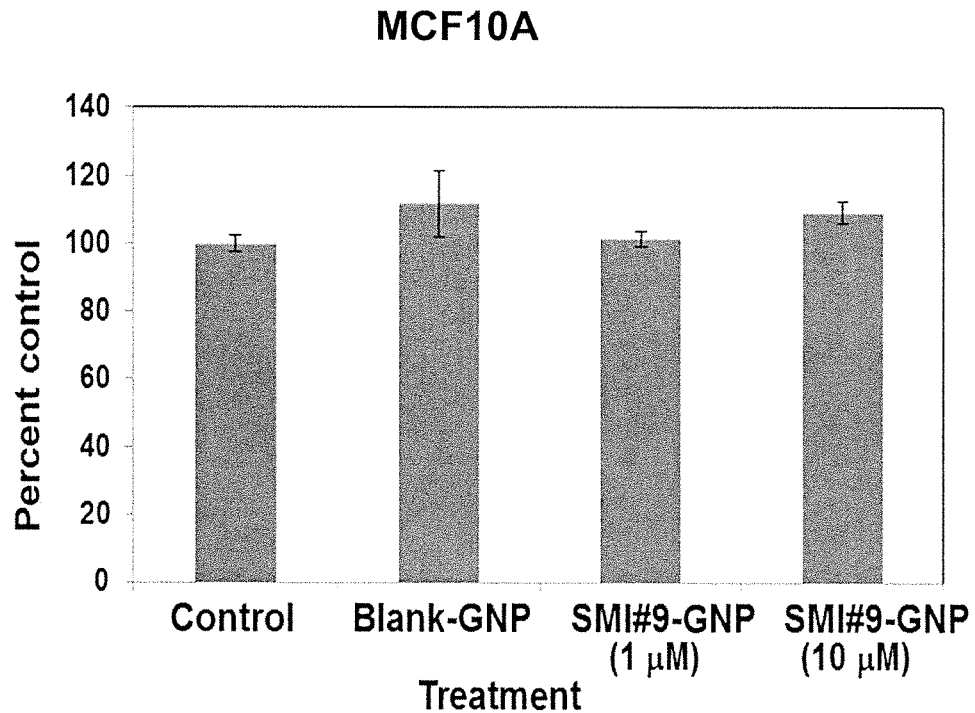
FIG. 4E is a graph showing nontransformed MCF10A human breast cells were unaffected by free SMI #9 and SMI #9-GNP.
FIG. 4F is a table showing that SMI #9-GNP synergistically increased cisplatin sensitivity of MDA-MB-468 and HCC1937 cells.
Figure 5A:
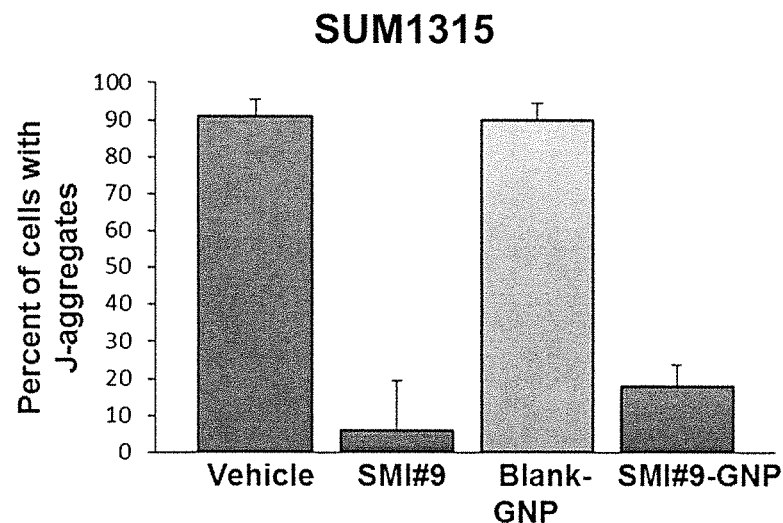
FIG. 5A is a graph showing that mitochondrial integrities of SUM1315 cells treated with free SMI #9 and SMI #9-GNP were similarly and dramatically compromised.

Consistent with MTT data shown in FIG. 4A, SMI #9-GNP treatment triggered morphological changes consistent with apoptosis in SUM1315 cells, shown in FIG. 5A. Early apoptosis marked by intercalated acridine orange within fragmented DNA and late stages of apoptosis marked by apoptotic body separation and presence of reddish-orange color due to acridine orange binding to fragmented DNA were observed in cells treated with SMI #9-GNP. SUM1315 cells treated with blank-GNP, at amounts equivalent to 5 µM SMI #9-GNP, were minimally affected as >98% of the cells showed an intact nuclear structure. Acridine orange/ethidium bromide staining of MDA-MB-231 cells showed similar SMI #9-GNP induced morphological changes. Consistent with the MTT data in FIG. 4C, acridine orange/ethidium bromide staining showed no morphological alterations with SMI #9-GNP confirming the lack of SMI #9-GNP sensitivity in HCC1937 cells.

Mitochondrial Assay

The impact of free SMI #9 or SMI #9-GNP on mitochondrial membrane potential ($\Delta\psi m$) on SUM1315 and HCC1937 TNBC cells was assessed using JC-1 (Mitocapture, Biovision, Mountainview, Calif.), a potentiometric green fluorescent dye that shifts to red fluorescence within mitochondria with a normal negative Am. Briefly, cells were incubated with the MitoCapture reagent for 15 min at 37° C. and imaged by fluorescence microscopy as described in Shekhar M P et al., Cancer Biol Ther 2008; 7:1774-82.

The percent of cells showing punctate red fluorescence or diffuse green fluorescence were scored by counting three-five fields of 50-100 cells in each field. Each experiment was repeated at least three times and results expressed as mean±S.E. Statistical significance of differences was determined by Student's t test.

SMI #9-GNP Sensitive TNBC Cells Show Altered Mitochondrial Membrane Potential

Figure 5B:
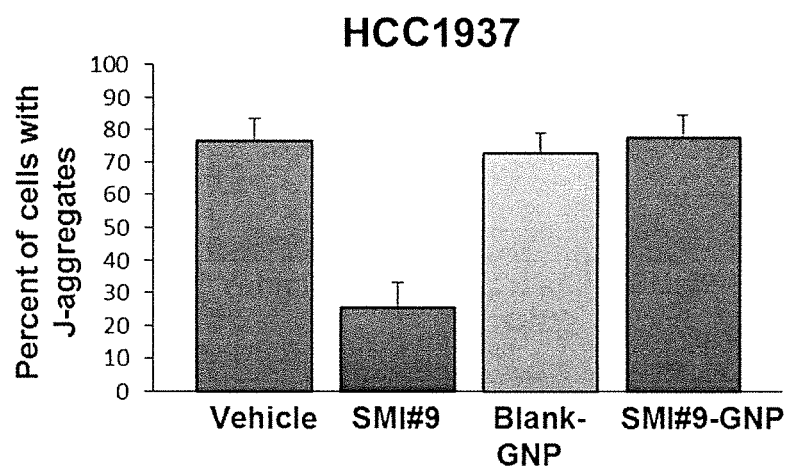
FIG. 5B is a graph showing that Δψm of HCC1937 cells were unaffected by SMI #9-GNP treatment.

Since the results of acridine orange/ethidium bromide staining showed morphological alterations consistent with apoptosis in SMI #9-GNP sensitive cells, assays were performed to determine whether this occurred by a mitochondrial-regulated mechanism. Alterations in mitochondrial transmembrane potential were evaluated in SUM1315 and HCC1937 cells treated with free SMI #9, blank-GNP, or SMI #9-GNP using the JC-1 assay. $\Delta\psi m$ is an important marker of mitochondrial function and has been used to monitor loss of mitochondrial function. JC-1 (5,5',6,6'-tetrachloro-1,1',3,3'-tetraethylbenzimidazolylcarbocynane iodide) is a lipophilic cationic dye which depending upon $\Delta\psi m$ accumulates in the cytoplasm as a green monomer or as punctate red aggregates in hyperpolarized mitochondria of cancer cells. The negative charge established by the mitochondrial membrane potential allows the lipophilic cationic dye to enter mitochondria where it accumulates. When a critical concentration is exceeded, JC-1-aggregates form, which fluoresces red. In apoptotic cells, Am collapses, and the JC-1 is unable to accumulate in mitochondria. JC-1 thus remains in the cytoplasm as a green fluorescent monomer. Untreated or blank-GNP treated control SUM1315 and HCC1937 cells show heterogeneous punctate red and green fluorescence. Overnight treatment with 1 µM free SMI #9 reduced the punctate red fluorescence staining in both SUM1315 and HCC1937 cells. Mitochondrial membrane depolarization consistent with a shift in fluorescence emission of JC-1 from red to green, and occasional cells with mislocalized punctate red signals were observed in HCC1937 cells treated with free SMI #9. However, consistent with the data from MTT and acridine orange/ethidium bromide staining, Am of HCC1937 cells were unaffected by SMI #9-GNP treatment as shown in FIG. 5B. In contrast, the mitochondrial integrities of SUM1315 cells treated with free SMI #9 and SMI #9-GNP were similarly and dramatically compromised as shown in FIG. 5A. These data indicate that SMI #9-induced cell death occurs from loss of mitochondrial function, and importantly free and conjugated SMI #9 behave similarly to inhibit mitochondrial function and cell viability.

Intracellular Uptake of SMI #9-GNP

To examine subcellular localization of the SMI #9-GNP transported into lysosomes, SUM1315 or HCC1937 cells were seeded on sterile coverslips and treated with blank- or SMI #9-GNP. Cultures were rinsed and then incubated in LysoSensor Green DND-189 (75 nM) for 30 min at 37° C. Cells were counterstained with 4',6-diamidino-2-phenylindole (DAPI) followed by imaging with Olympus BX40 fluorescence microscope.

Lysosomal Uptake of SMI #9-GNP

Since SUM1315 and HCC1937 breast cancer cells displayed different sensitivities to SMI #9-GNP while maintaining similar cellular sensitivities to free SMI #9, it was hypothesized that these variations presumably arose from differences in uptake rather than intracellular processing. Internalization of nanoparticles in general is accomplished by endocytosis, transfer of cargo to early and mature endosomes, and fusion to become late endosomes/lysosomes. Control or SMI #9-GNP treated SUM1315 or HCC1937 cells were stained with LysoSensor Green DND-189 to label the lysosomes and the presence of aggregated GNP cargo examined. LysoSensor Green DND-189 is an acidotropic dye that accumulates in intracellular acidic organelles as a result of protonation and has a fluorescence intensity that is proportional to acidity. SMI #9-GNP is efficiently internalized into SUM1315 cells as evidenced by the presence of GNP aggregates colocalizing with lysosomes marked by the LysoSensor Green DND-189 dye. The overlapping of lysosomes with GNP aggregates and the strong sensitivity of SUM1315 cells to SMI #9-GNP indicate hydrolysis of the ester bond linked SMI #9-GNP and release of conjugated SMI #9 as supported by FTIR and LC-MS/MS analysis shown in FIGS. 2 and 3. Although both control and SMI #9-GNP treated SUM1315 cells showed robust staining with the lysosomal marker, the formation of "acidic vesicles" was observed only in SMI #9-GNP treated SUM1315 cells. In contrast, HCC1937 cells showed weak staining with LysoSensor Green, indicating weak acidification.

Western Blot and Immunofluorescence Analysis

Breast cancer cells treated with vehicle, free SMI #9, blank- or SMI #9-GNP (1-5 µM) for 24-96 hours were lysed, and aliquots of lysates containing 25 µg of protein were subjected to SDS-PAGE and western blot analysis of PARP-1 (Cell Signaling), Rad6, LC3-I/II (Cell Signaling), and 3-actin (Sigma). To determine LC3 subcellular localization, control or SMI #9-GNP treated cells were fixed with methanol:acetone (1:1, v/v) and stained with anti-LC3 antibody. Slides were incubated with FITC-conjugated secondary antibody, counterstained with DAPI and analyzed by fluorescence microscopy.

SMI #9-Induced Cell Death is Associated with PARP-1 Stabilization

Figure 6A:
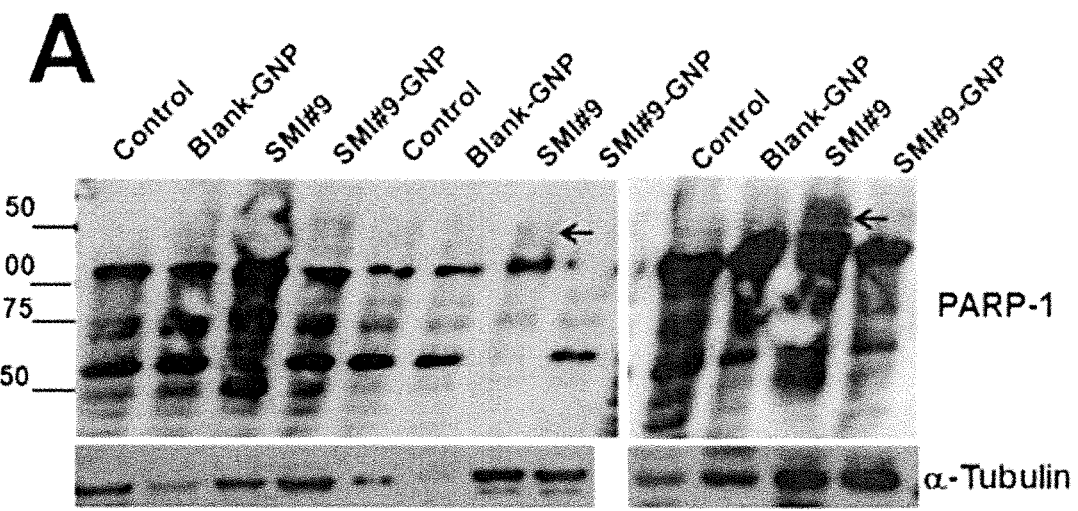
FIG. 6A is an image of Western immunoblots showing results of analysis of steady-state levels of PARP-1 protein in TNBC cells treated for 24 hours with vehicle, free SMI #9, blank-GNP or SMI #9-GNP.
Figure 6B:
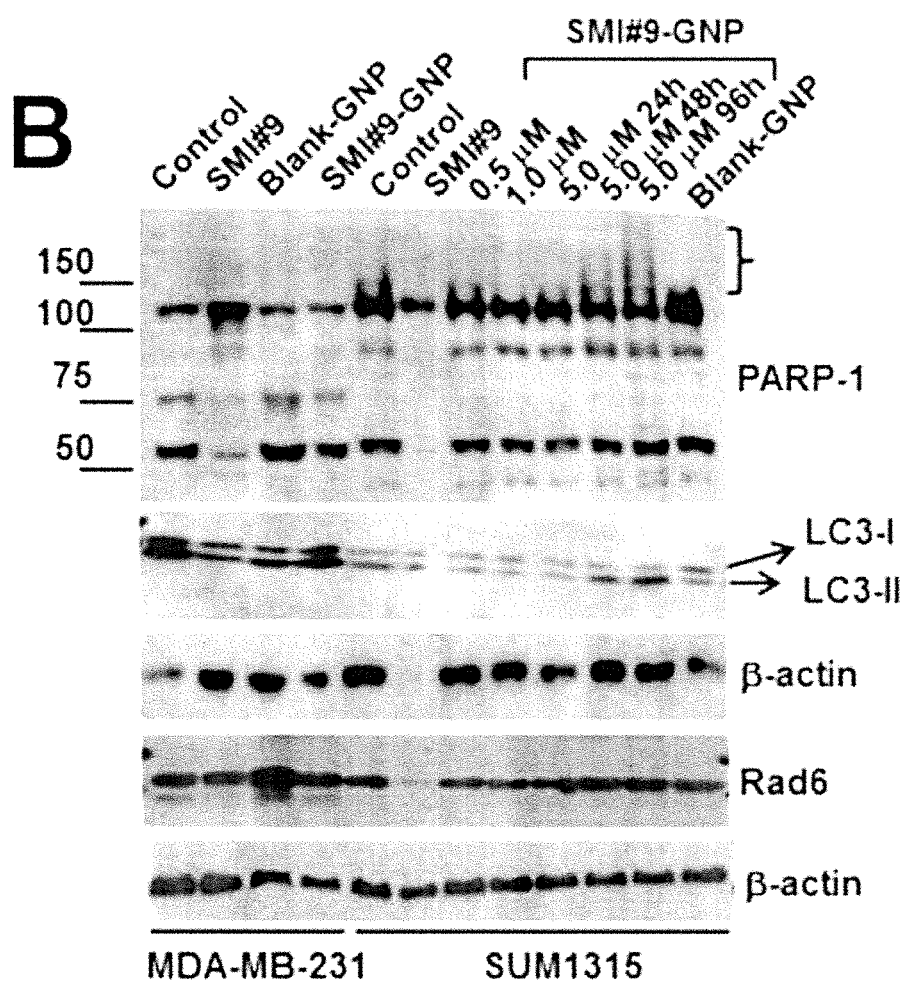
FIG. 6B is an image of Western immunoblots showing results of analysis of steady-state levels of PARP-1 protein, LC3-I, LC3-II, Rad6 in TNBC cells treated for 24 to 96 hours with vehicle, free SMI #9, blank-GNP or SMI #9-GNP.

Since SMI #9 treatment induces apoptosis by causing mitochondrial dysfunction, the steady-state levels of PARP-1 protein in TNBC cells treated for 24 h with vehicle, free SMI #9, blank-GNP or SMI #9-GNP were analyzed. As shown in FIG. 6A, each cell line displayed unique PARP-1 processing blueprints, which was unaffected by blank-GNP and SMI #9-GNP. However, treatment with free SMI #9 for 24 hours, resulted in stabilization/hyperactivation of PARP-1. Accumulation of PARP-1 containing heterogeneous chain lengths of poly ADP-ribose (PARylated PARP-1) was observed in all cell lines that appear to result from alterations in PARP-1 processing, shown in FIG. 6A. Since 24 hour treatment with SMI #9-GNP did not evoke similar changes in PARP-1, PARP-1 analysis in SUM1315 cells treated with SMI #9-GNP for 24-96 hours was performed. The results in FIG. 6B show that, like free SMI #9, SMI #9-GNP also induces PARP-1 activation as evidenced by time-dependent accumulation of high molecular weight PARP-1 forms after 24 hours. These data indicate that both free and conjugated SMI #9 exert similar molecular effects on PARP-1 activation; however, GNP-conjugated SMI #9 requires longer time to elicit this effect.

The conversion of the soluble form of LC3 (LC3-I) to the lipidated and autophagosome-associated form (LC3-II) is considered one of the hallmarks of autophagy. High basal levels of both LC3-I and LC3-II were observed in MDA-MB-231 cells compared to SUM1315 cells, indicating the involvement of autophagic flux in normal survival of these cells as shown in FIG. 6B. Treatment for 24 hours with free SMI #9 but not SMI #9-GNP downregulated both LC3-I and LC3-II in MDA-MB-231 cells, shown in FIG. 6B. Although changes in LC3-I processing was not readily apparent in SUM1315 cells treated for 24 h with free SMI #9 or SMI #9-GNP, a dramatic increase in LC3-I to LC3-II conversion that was commensurate with PARP-1 hyperactivation was observed at 48 and 96 hours of treatment as shown in FIG. 6B. These effects are selective for SMI #9-GNP since treatment with blank-GNP for up to 96 hours produced no changes in LC-3-I/II ratios or PARP-1 activation as shown in FIG. 6B. The coincident increases in PARP-1 hyperactivation and LC-I to LC3-II conversion in SMI #9-GNP treated SUM1315 cells signify autophagic cell death as supported by MTT assays, shown in FIG. 4A, phase contrast microscopy, presence of lysosome-associated acidic vesicles, and LC3-positive dots in SMI #9-GNP treated but not control cells. Rad6 steady-state levels were slightly increased in SUM1315 cells treated with SMI #9-GNP for 24-96 hours shown in FIG. 6B. Since Rad6 activity is inhibited under these conditions, these data indicate an important role for Rad6 in assuring survival of cancer cells.

Fluorescence Image Processing

Images were captured with a fluorescence microscope using the same color intensity threshold for all treatments. At least 4-8 fields (minimum of 50 cells) were analyzed and representative images shown. All images were compiled using Adobe Photoshop using the same contrast adjustment applied to all images.

Statistical Analysis

Each experiment was performed in triplicate and reproduced at least three times. Data are expressed as mean values±standard deviation, and differences were considered to be statistically significant when the P value determined by Student's t-test was <0.05.

Pharmacokinetic (PK) Analysis

Figure 7:
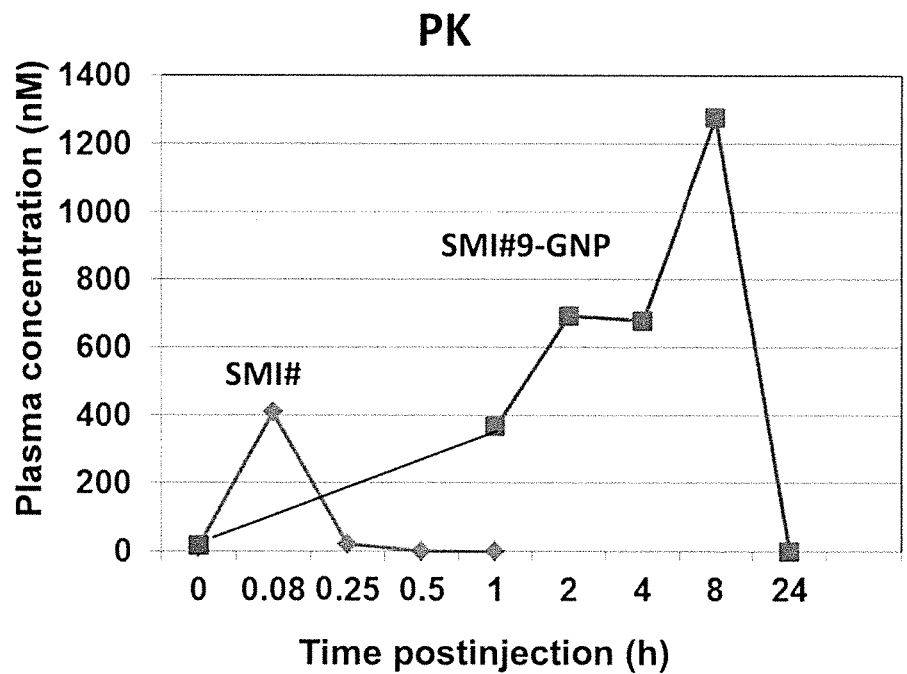
FIG. 7 is a graph showing comparison of pharmacokinetic profiles of free parent SMI #9 vs. SMI #9-GNP.

To determine release of conjugated drugs and metabolic stability of GNP conjugates, mice were given a single i.v. injection of SMI #9-GNP at 5 mg/kg body wt. Blood samples were collected at 0, 5 min, 15 min, 30 min, 1 h, 2 h, 4 h, 8 h, and 24 h post-injection. Similarly, to assess the stability of SMI #9 as a free drug, a single i.v. injection of SMI #9 at 5 mg/kg was injected and blood samples collected. Concentrations of SMI #9 in plasma were determined by tandem LC-MS/MS and non-compartmental analysis with WinNonlin v5.2 (Pharsight). PK experiments comparing the PK profiles of free parent SMI #9 vs. SMI #9-GNP showed that free SMI #9 has poor in vivo drug exposure (Cmax 409 nM; Tmax ~5 min) which is significantly enhanced when SMI #9 is administered as a nanoconjugate (Cmax 1276 nM; Tmax ~≥8 h), FIG. 7. These data demonstrate that pharmacologically relevant concentrations of SMI #9 are achieved by i.v. injection.

Orthotopic Tumor Growth Assays

MDA-MB-468 or SUM1315 triple negative breast cancer cells ($1 \times 10^6$ cells suspended in 0.1 ml Matrigel) were injected subcutaneously into the fatpads of fourth and fifth inguinal mammary glands of female nude mice. Mice were randomized and treatments with SMI #9-GNP (0.285 mg/kg body wt), SMI #9 free drug (1.5 mg/kg body wt.), blank-GNP (volumes equivalent to SMI #9-GNP), or vehicle control were initiated upon detection of palpable lesions. Control vehicle or SMI #9 free drug was administered intratumorally whereas blank-GNP and SMI #9-GNP were administered intraperitoneally. Treatments were given every fourth day. Tumor volumes and body weights were measured twice a week and mice were monitored for weight loss, gastrointestinal distress, activity, body posture, and food/water intake. Mice were sacrificed at 35-44 days post-implantation. Tumors were harvested and weighed.

Figure 8:
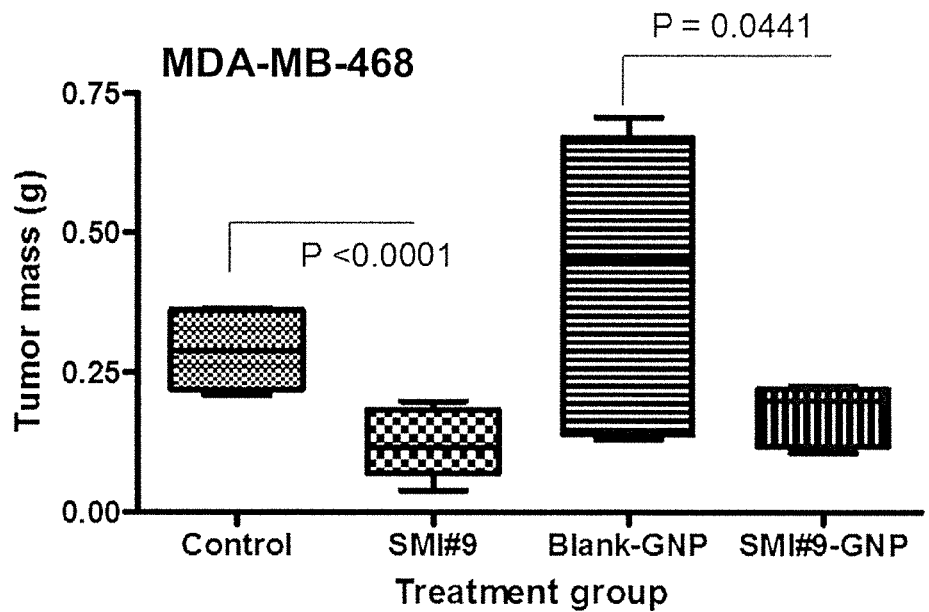
FIG. 8 is a graph showing results of treatment of MDA-MB-468 triple negative breast cancer cell derived tumors in mice with SMI #9-GNP compared to treatment of MDA-MB-468 tumors with "blank-GNP," i.e. no SMI #9.
Figure 9:
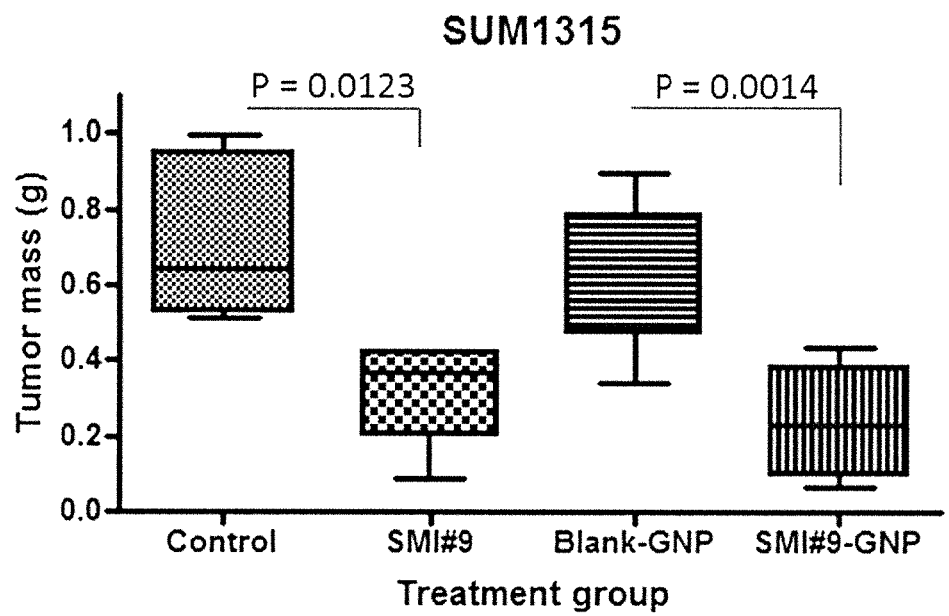
FIG. 9 is a graph showing results of treatment of SUM1315 triple negative breast cancer cell derived tumors in mice with SMI #9-GNP compared to treatment of SUM1315 tumors with "blank-GNP," i.e. no SMI #9.
Figure 10:
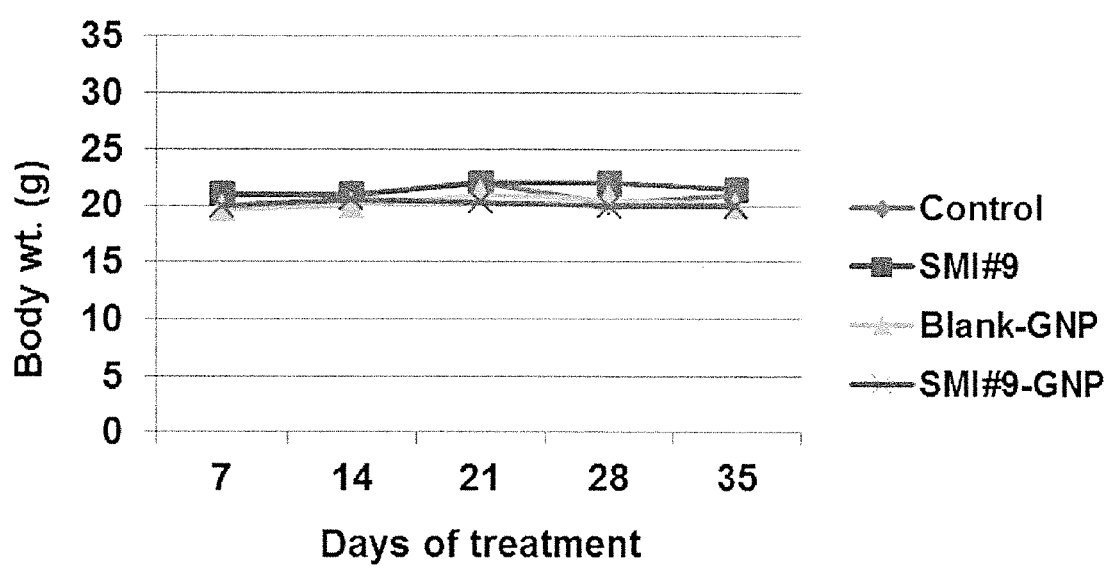
FIG. 10 is a graph showing that although SMI #9-GNP treatment induced significant tumor growth inhibition, the treatment was not toxic as these mice showed no significant differences in their body weights, activity, body posture and food/water intake compared to controls.

SMI #9-GNP treated mice showed significant reductions in growth of both MDA-MB-468 (P=0.04) and SUM1315 (P=0.001) derived tumors compared to tumors in mice receiving blank-GNP, FIGS. 8 and 9. Although the tumors in mice that received SMI #9 free drug showed tumor growth inhibition compared to controls, it must be noted that in this case the drug had to be injected intratumorally rather than systemically as in the case of SMI #9-GNP. Mice bearing SUM1315 xenografts that received intraperitoneal injection of SMI #9 free drug at 5 mg/kg showed no significant change in tumor growth compared to controls. Although SMI #9-GNP treatment induced significant tumor growth inhibition, the treatment was not toxic as these mice showed no significant differences in their body weights, activity, body posture and food/water intake compared to controls, FIG. 10.

Melanoma Cell Sensitivity to SMI #9-GNP

Figure 11:
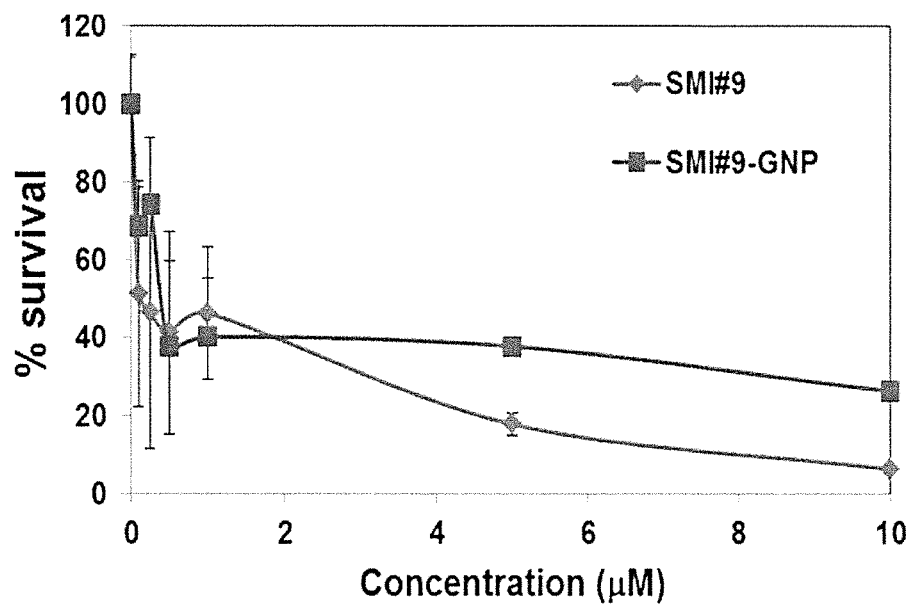
FIG. 11 is a graph showing that SMI #9-GNP decreased survival of M14 cells (GI50 0.5 μM) while similar treatment with blank-GNP added at amounts equivalent to 1 or 10 μM demonstrated negligible cytotoxicity.
Figure 12:
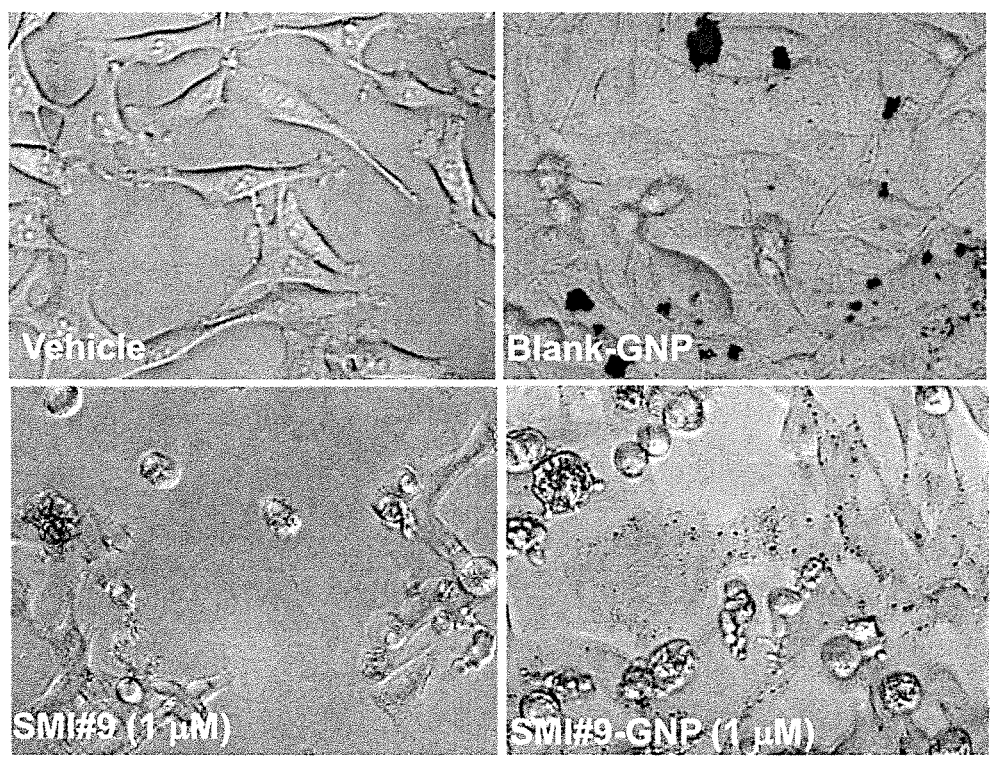
FIG. 12 shows images indicating that, consistent with the MTT assay results, simultaneous phase-contrast imaging confirmed SMI #9-GNP-induced morphologic transformations consistent with cell sensitization, and lack thereof with blank-GNP.

M14 melanoma cells were maintained in Dulbecco's Modified Eagle's Medium (DMEM)/F-12 supplemented with 5% fetal bovine serum. SMI #9-GNP sensitivity was assessed by MTT assay. Cells ($5\times10^3$) were seeded in 96-well plates and treated with free SMI #9, SMI #9-GNP, or blank-GNP at various concentrations in triplicates for 72 h. On the final day, medium was replaced with drug-free medium, and incubated with MTT for 2-3 h. MTT-formazan crystals were dissolved in 0.04 N HCl/isopropanol and absorbance measured at 570 nm using the Synergy 2 microplate reader. At least three independent experiments were performed for each cell line. SMI #9-GNP decreased survival of M14 cells (GI50 0.5 µM), FIG. 11, similar treatment with blank-GNP added at amounts equivalent to 1 or 10 µM demonstrated negligible cytotoxicity. Consistent with the MTT assay results, simultaneous phase-contrast imaging confirmed drug-induced morphologic transformations consistent with cell sensitization but not with blank-GNP as shown in FIG. 12.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A pharmaceutical composition, comprising:

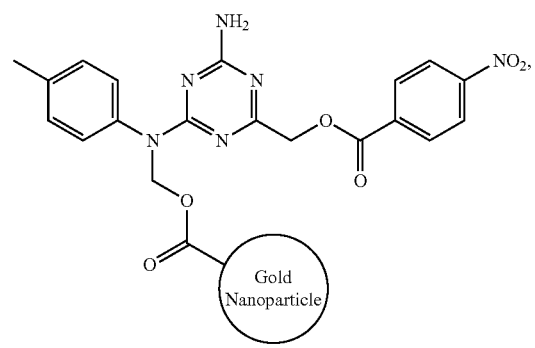

-continued

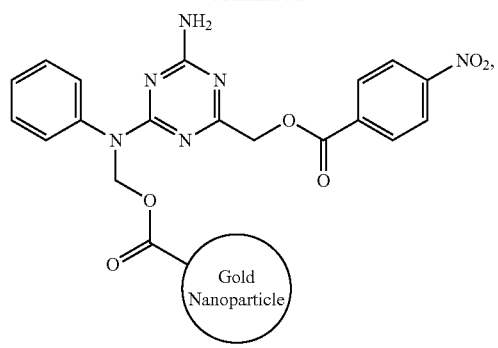

or a pharmaceutically acceptable salt of either thereof.

2. The pharmaceutical composition of claim 1, further comprising a pharmaceutically acceptable carrier.

3. The pharmaceutical composition of claim 1, further comprising an additional therapeutic agent.

4. The pharmaceutical composition of claim 3, wherein the additional therapeutic agent is coupled to the gold nanoparticle.

5. The pharmaceutical composition of claim 3, wherein the additional therapeutic agent is an anti-cancer agent.

6. A method of treating a subject having cancer characterized by overexpression and/or overactivity Rad6, comprising:
    administering a therapeutically effective dose of the pharmaceutical composition according to claim 1.

7. The method of claim 6, further comprising administering an additional therapeutic agent.

8. The method of claim 7, wherein the additional therapeutic agent is coupled to the gold nanoparticle.

9. The method of claim 6, wherein the cancer is melanoma.

10. The method of claim 6, wherein the cancer is breast cancer.

11. The method of claim 6, wherein the cancer is triple negative breast cancer.

12. The method of claim 6, wherein the cancer is characterized by resistance to an anti-cancer agent.

13. A commercial package, comprising:

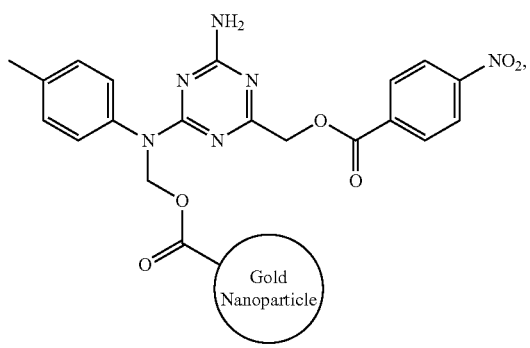

-continued

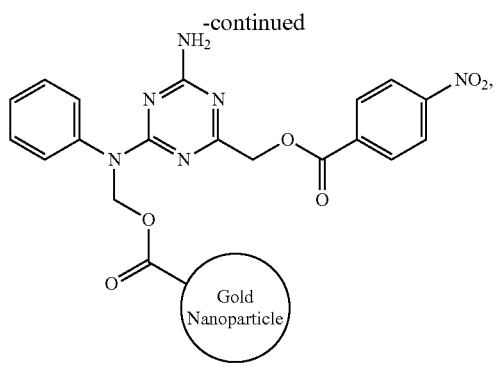

or a pharmaceutically acceptable salt of either thereof.

14. The commercial package of claim 13, further comprising a pharmaceutically acceptable carrier.

15. The commercial package of claim 13, further comprising an additional therapeutic agent.

16. The commercial package of claim 15, wherein the additional therapeutic agent is coupled to the gold nanoparticle.

17. The commercial package of claim 15, wherein the additional therapeutic agent is an anti-cancer agent.

* * * * *